(12) United States Patent
Canaani et al.

(10) Patent No.: US 6,861,220 B2
(45) Date of Patent: Mar. 1, 2005

(54) GENETIC SCREENING METHODS

(75) Inventors: Dan Canaani, Ra'anana (IL); Arnold Simons, Carcur (IL); Naomi Dafni, Keisaria (IL); Iris Dotan, Tel Aviv (IL)

(73) Assignee: Ramot University Authority for Applied Research & Industrial Development LTD, Tel Aviv (IL)

( * ) Notice: Subject to any disclaimer, the term of this patent is extended or adjusted under 35 U.S.C. 154(b) by 141 days.

(21) Appl. No.: 09/975,300

(22) Filed: Oct. 12, 2001

(65) Prior Publication Data

US 2002/0123034 A1 Sep. 5, 2002

Related U.S. Application Data

(63) Continuation-in-part of application No. 09/391,444, filed on Sep. 8, 1999, now Pat. No. 6,569,623.

(51) Int. Cl.$^7$ .......................... C12Q 1/68; C12N 15/74; C07H 21/02
(52) U.S. Cl. .......................... 435/6; 435/29; 435/320.1; 435/481; 435/DIG. 1; 435/DIG. 2; 435/DIG. 3; 435/DIG. 9; 435/69.1; 530/350; 536/23.5; 536/23.1; 536/25.32; 536/23.4; 536/18.7
(58) Field of Search .......................... 435/6, 471, 476, 435/29, 320.1, 69.1, 481, DIG. 1, DIG. 2, DIG. 3, DIG. 9; 530/350; 536/23.1, 23.5, 187, 23.4, 25.32

(56) References Cited

U.S. PATENT DOCUMENTS

| 4,686,186 A | 8/1987 | Sugden |
| 5,168,062 A | 12/1992 | Stinski |
| 5,625,048 A | 4/1997 | Tsien et al. |

OTHER PUBLICATIONS

Deiss et al., Science, vol. 252, pp. 117–120, Apr. 1991.*
Wade–Martins et al., Nucleic acid Research, vol. 27, No. 7, pp. 1674–1682, 1999.*
Simons A, Dafni N., Dotan I., Oron Y., Canaani D., "Establishment of a Chemical Synthetic Lethality Screen in Cultured Human Cells," Genome Research p. 266 www.genome.org/cgi/doi/10.1101/gr.154201.

Yates, J., Warren N. Sugden B., "Stable replications of plasmids derived from Epstein–Barr virus in various mammalian cells" Nature vol. 313 2B Feb. 1985.

Zhu Z., Geertruida M., Veldman., Cowie A., Carr A., Schaffhausen B., Kamen R., "Construction and Functional Characterization of Polyomavirus genomes that separately encode the three early proteins" Journal of Virology, Jul. 1984 p. 170–180 vol. 51 1984.

Gonzalez J.E., Negulescu P.A., "Intracellular detection assays for high throughput screening" Current opinion in Biotechnology 1998, 9:624–631.

* cited by examiner

*Primary Examiner*—Padmashri Ponnaluri
(74) *Attorney, Agent, or Firm*—Eitan, Pearl, Latzer & Cohen Zedek, LLP; Mark S. Cohen

(57) ABSTRACT

A method for screening molecule which have a synthetic lethal property when in combination with a gene of interest carrying a non-lethal mutation, said method comprising the steps of: transfecting a first reporter gene into mammalian cells having a genome comprising a gene of interest which carries a non-lethal mutation, or a genome which is null of said gene of interest; selecting clones stably expressing said fist reporter gene; introducing into said cells a survival plasmid comprising a functioning copy of said gene of interest, a second reporter gene, selectable marker, an origin of DNA replication and a nuclear antigen gene essential for replication of the plasmid within said cells, wherein said survivsal plasmid is autonomously replicating and spontaneously lost from said cells; growing said cells in the presence of a selection compound which selects for said selectable marker; selecting cell clones stably expressing said second reporter gene and said functioning copy of said gene of interest; removing selection for the selectable marker, and adding molecules destined for screening of their ability to impose selective pressure enforcing retention of the unstable survival plasmid, determining survival plasmid retention in cells, thus identifying a molecule having a synthetic lethal property when in combination with non lethal mutated gene of interest.

8 Claims, 11 Drawing Sheets

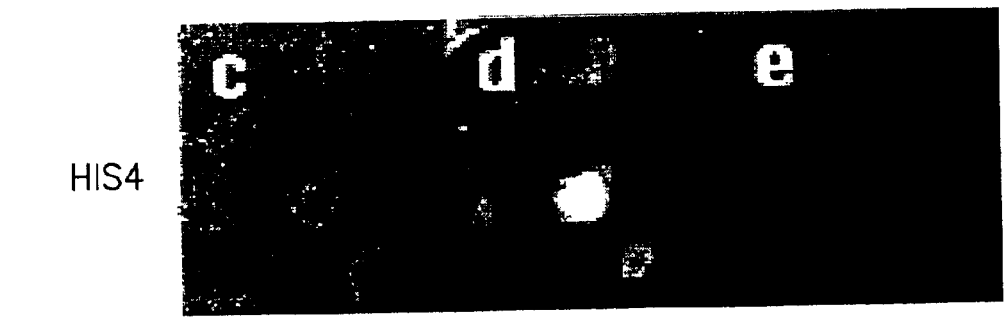
HIS4
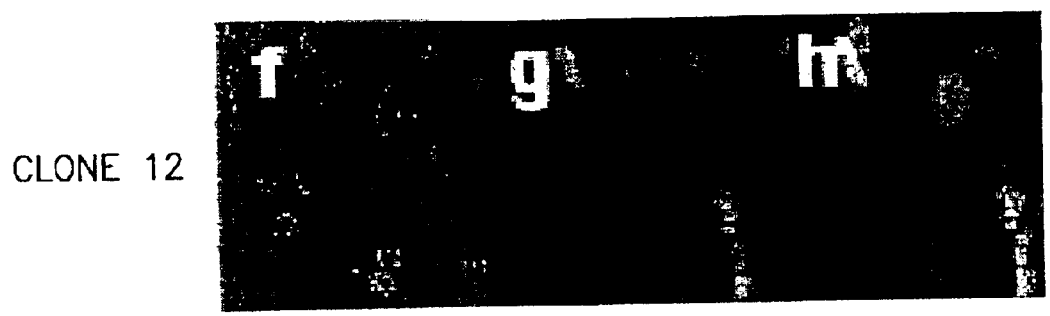
CLONE 12
FIG.3

GENETIC SCREENING METHODS

This application is a Continuation-in Part Application of U.S. Ser. No. 09/391,444, filed Sep. 8, 1999, now U.S. Pat. No. 6,569,623 which is incorporated herein by reference.

BACKGROUND OF THE INVENTION

With continued progress in the Human Genome Project as well as the initiation of the Mouse/Rat Genome Projects, and the sequencing of the majority of the human cDNAs, the elucidation of gene function has become a major priority. High throughput screening methods are required in order to determine the functions of large numbers of genes in an efficient manner. Screening methods are also required for discovering novel gene-specific drugs. In the search for such drugs, it would be advantageous to be able to elucidate the interaction between specific chemical reagents and one or more genes in a high throughput format. This is particularly relevant with respect to cancer drugs.

A synthetic or synergistic lethality screening method has previously been described in yeast cells (1,2). The essence of this screen in yeast, is the ability to identify nonallelic and nonessential mutations that are lethal in combination with a nonessential mutation in a gene of interest (i. e. synthetic lethality). A wild-type copy of the gene of interest, on an episomal plasmid, is introduced into cells which are null for expression of this gene. Random chemical mutagenesis of the entire yeast genome within these cells may inactivate a gene which is synthetically lethal with the gene of interest. Under these conditions, retention of the plasmid, which is otherwise spontaneously lost, and expression of the gene of interest become essential for survival. Plasmid loss or retention is detected by changes in colony pigmentation, due to the presence on the plasmid of a wild-type gene whose product is essential for red pigment accumulation (3).

This genetic method is very powerful as it can reveal not only interactions between gene products with direct physical contacts, but also interactions along the same or parallel pathways.

SUMMARY OF THE INVENTION

This invention provides a screening method useful in identifying molecules having gene-specific cell-lethal properties. A further object of the present invention is to provide a screening method useful in isolating genes and identifying unknown functions of genes or unknown functional links between genes.

In one embodiment there is provided a method for screening molecule which have a synthetic lethal property when in combination with a gene of interest carrying a non-lethal mutation, the method comprising the steps of: i. transfecting a first reporter gene into amammalian cells having a genome comprising a gene of interest which carries a non-lethal mutation, or a genome which is null of the gene of interest; ii. selecting clones stably expressing the first reporter gene; iii. introducing into the cells a survival plasmid comprising a functioning copy of the gene of interest, a second reporter gene, selectable marker, an origin of DNA replication and a nuclear antigen gene essential for replication of the plasmid within the cells, wherein the survivsal plasmid is autonomically replicated and spontaneously lost from the cells; vi.growing the cells in the presence of a selection compound which selects for the selectable marker; vii. selecting cell clones stably expressing the second reporter gene and the functioning copy of the gene of interest; viii. adding molecules for screening of their ability to impose selective pressure for the retention of the spontaneously lost survival plasmid (thus preventing the synthetic lethality between the resident mutant gene of interest and the added molecule) to the cell clones of step V. ix. determining survival plasmid retention in cells, thus identifying a molecule having a synthetic lethal property when in combination with non lethal mutated gene of interest.

In another embodiment there is provided a method for screening a cDNA molecule, which have a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. selecting cell clones stably expressing the second reporter gene and the functioning copy of the gene of interest; vi. incorporating the cDNA molecule—into a vector vehicle containing a second selectable marker gene so as to obtain a vector vehicle-cDNA molecule. vii. transfecting cells with vector vehicles-cDNA molecule while removing selection for the first selectable marker, and instituting selection for pools of cells expressing the second selectable marker gene. viii. determining survival plasmid retention in cells, thus identifying a cDNA having a synthetic lethal property when in combination with non lethal mutated gene of interest.

In another embodiment there is provided a method for screening a drug (this is a private case of a molecule or a chemical reagent) which have a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. selecting cell clones stably expressing the second reporter gene and the functioning copy of the gene of interest; vi. adding the drug for screening of their ability to impose selective pressure for the retention of the spontaneously lost survival plasmid to the cell clones of step V. vii.

determining survival plasmid retention in cells, thus identifying a drug having a which have a synthetic lethal property when in combination with non lethal mutated gene of interest.

In another embodiment there is provided a method for screening a chemical agent which which have a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. adding the chemical agent for screening of its ability to impose selective pressure for the retention of the spontaneously lost survival plasmid to the cell clones of step V. vi. selecting cell clones stably expressing the second reporter gene and the functioning copy of the gene of interest; vii. Determining survival plasmid retention in cells which survive, thus identifying a chemical agent which have a synthetic lethal property when in combination with non lethal mutated gene of interest.

In another embodiment there is provided a method for screening a library comprising a plurality of molecules in order to identify molecule/s having a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; vi. growing the cells in the presence of a selection compound which selects for the selectable marker; v. selecting cell clones stably expressing the second reporter gene and the functioning copy of the gene of interest; vi. adding the library comprising a plurality of molecules for screening of its ability to impose selective pressure for the retention of the spontaneously lost survival plasmid to the cell clones of step V. vii. determining survival plasmid retention in cells, thus identifying a library comprising a plurality of molecules having a synthetic lethal property when in combination with non lethal mutated gene of interest.

In another embodiment there is provided a method for screening molecule which have a synthetic lethal property when in combination with a mutant or normal gene of interest which is overexpressed, the method comprising the steps of: i. transfecting a first reporter gene into mammalian cells having a genome comprising a mutant or normal gene of interest which is overexpressed, ii. selecting clones stably expressing the first reporter gene; iii.

introducing into the cells a survival plasmid comprising a dominant-negative mutant of the gene of interest, a second reporter gene, selectable marker, an origin of DNA replication and a nuclear antigen gene essential for replication of the plasmid within the cells, wherein the survivsal plasmid is autonomously replicating and spontaneously lost from the cells; vi.

growing the cells in the presence of a selection compound which selects for the selectable marker; vii. selecting cell clones stably expressing the second reporter gene and the dominant-negative mutant of the gene of interest; viii. removing selection for the selectable marker, and adding molecules destined for screening of their ability to impose selective pressure enforcing retention of the unstable survival plasmid. ix. determining survival plasmid retention in cells, thus identifying a molecule having a synthetic lethal property when in combination with the a mutant or normal gene of interest which is overexpressed.

In another embodiment there is provided a method for screening a cDNA molecule, which have a synthetic lethal property when in combination with a mutant or normal gene of interest which is overexpressed, the method comprising the steps of: i. transfecting a first reporter gene into a mammalian cells having a genome comprising a mutant or normal gene of interest which is overexpressed; ii. selecting clones stably expressing the first reporter gene;

iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the plasmid is spontaneously lost from the cells; iv.growing the cells in the presence of a selection compound which selects for the selectable marker; v. selecting cell clones stably expressing the second reporter gene and the dominant-negative mutant of the gene of interest; vi.

incorporating the cDNA molecule—into a vector vehicle containing a second selectable marker gene so as to obtain a vector vehicle-cDNA molecule. vii. transfecting cells with vector vehicles-cDNAs molecules while removing selection for the first selectable marker, and instituting selection for pools of cells expressing the second selectable marker gene. viii.

determining survival plasmid retention in cells, thus identifying a cDNA having a synthetic lethal property when in combination with the a mutantor normal gene of interest which is overexpressed.

In another embodiment there is provided a method for screening a drug which have a synthetic lethal property when in combination with a mutant or normal gene of interest which is overexpressed, the method comprising the steps of: i. transfecting a first reporter gene into a non-yeast eukaryotic cells having a genome comprising a mutant or normal gene of interest which is overexpressed; ii. selecting clones stably expressing the first reporter gene; iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the survival plasmid is spontaneously lost from the cells; iv. growing the cells in the presence of a selection compound which selects for the selectable marker; v. selecting cell clones stably expressing the second reporter gene and the dominant-negative mutant of the gene of interest; vi. adding the drugs destined for screening their ability to impose selective pressure enforcing retention of the spontaneously lost survival plasmid; vii. determining survival plasmid retention in cells, thus identifying a drug having a a synthetic lethal property when in combination with the mutant or normal gene of interest which is overexpressed.

In another embodiment there is provided a method for screening a library comprising a plurality of molecules which have a synthetic lethal property when in combination with a mutant or normal gene of interest which is overexpressed, the method comprising the steps of: i. transfecting a first reporter gene into mammalian cells having a genome comprising a mutant or normal gene of interest which is overexpressed; ii. selecting clones stably expressing the first reporter gene; iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the plasmid is spontaneously lost from the cells; vi. growing the cells in the presence of a selection compound which selects for the selectable marker; v. selecting cell clones stably expressing the second reporter gene and the dominant-negative mutant of the gene of interest; vi. adding the library comprising a plurality of molecules in order to identify those that impose selective pressure enforcing the retention of the spontaneously lost survival plasmid. vii. determining survival plasmid retention in cells, thus identifying at least one molecule within a library having a synthetic lethal property when in combination with the mutant or normal gene of interest which is overexpressed.

In another embodiment there is provided a kit for screening a molecule comprising a plurality of molecule types in mammalian cells having a genome, in order to identify a the molecule having a gene-specific lethal property in the cell, comprising: an integration plasmid comprising a first reporter gene; a survival plasmid compatible with a mammalian cell comprising a functional copy of a gene of interest or a dominant-negative mutant of a gene of interest, a second reporter gene, a dominant selectable marker gene, an origin of DNA replication and a nuclear antigen gene essential for replication of the survival plasmid, the survival plasmid being spontaneously lost from the cell.

In another embodiment there is provided a kit for screening a group of DNA molecules in order to identify among them one or more modulators of gene expression which are synergistically lethal to a mammalian cell together with a gene of interest, comprising: an integration plasmid comprising a first reporter gene; a survival plasmid compatible with a mammalian cell comprising a functional copy of a gene of interest or a dominant-negative mutant of a gene of interest, a second reporter gene, a dominant selectable marker gene, an origin of DNA replication and a nuclear antigen gene essential for replication of the survival plasmid, the survival plasmid being spontaneously lost from the cell; and a vector vehicle containing a second dominant selectable marker gene and carrying either a human GSE library or a wild-type cDNA library.

In another embodiment there is provided a survival plasmid compatible with a mammalian cell comprising a functional copy of a gene of interest, a reporter gene, a dominant selectable marker gene, an origin of DNA replication and a nuclear antigen gene essential for replication of the episome, the episome being spontaneously lost from the cell, wherein the product of the reporter gene is a mutant green fluorescent protein (GFP).

In another embodiment there is provided a survival plasmid compatible with a mammalian cell comprising a dominant-negative mutant of a gene of interest, a reporter gene, a dominant selectable marker gene, an origin of DNA replication, and a nuclear antigen gene essential for replication of the episome, the episome being spontaneously lost from the cell, wherein the product of the reporter gene is a mutant green fluorescent protein (GFP).

BRIEF DESCRIPTION OF THE DRAWINGS

The present invention will be understood and appreciated more fully from the following detailed description taken in conjunction with the appended drawings in which.

Arrows indicate the action of enzymes. The sites of inhibition by mycophenolic acid (MPA), ribavirin (RI), mizoribine (MI) and aminopterin are marked;

FIG. 2 illustrates the structure of the double labeled GFP plasmid system. (A) The pIS integrating sphGFP vector. (B) The HGPRT-tpzGFP survival plasmid. P-CMV, P-TK and P-RSV indicate the viral promoters of herpes TK1, CMV and RSV, respectively. IVS represents the rabbit globin second intron. PA stands for polyadenylation signal. Filled-in arrows indicate open reading frames translated in the transduced human cells. For construction details, see the Methods section.

FIG. 3 shows photographs and fluorescent images of vector transfected cells. (C-E) HIS4 cells expressing the pIS construct. (F-H) Clone 12 cells that express both the sphGFP from the pIS construct, and tpzGFP from the episomal survival plasmid. Panels C and F are photographs of the phase image. Fluorescent images in panels D, E, F and G were obtained using filter sets that preferentially detect sphGFP (D, G), or tpzGFP (E, H). The Clone 12 cells were maintained in hygromycin B selection to retain the survival plasmid. Microscopic images were captured using an Olympus BX40 microscope with a Sony CCD-Iris color video camera. SphGFP was visualized using a filter block with an excitation bandpass of 340–380 mn. TpzGFP was visualized using a filter block with an excitation bandpass of 450–490 mn.

Figure 4:
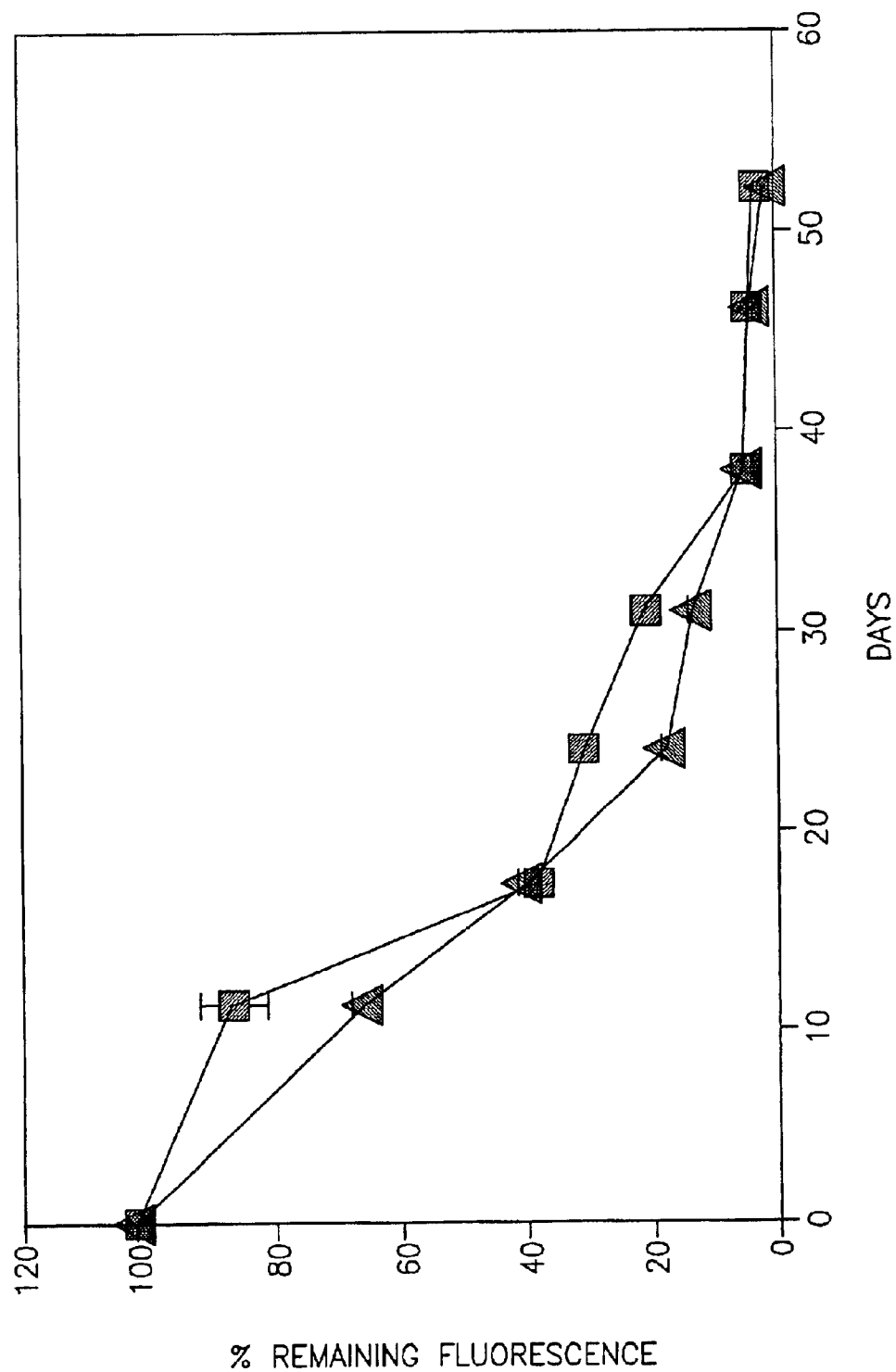

FIG. 4 shows spontaneous loss of tpzGFP-marked survival plasmid in Clone 12 cells. Cells were maintained in 96 well plates over the entire time period (rectangles), or grown by continuous passaging in 90 mm petri dishes (triangles). Passaged cells were trypsinized and seeded into microplates on the day of reading. Plates were read using a microplate fluorescence reader (see Methods section). Data points show the mean relative fluorescence ratio between tpzGFP and sphGFP, express as a percentage of the same ratio measured from cells maintained under hygromycin B selection. All data represent the mean of fluorescence reading from at least 3 wells.

Figure 5:
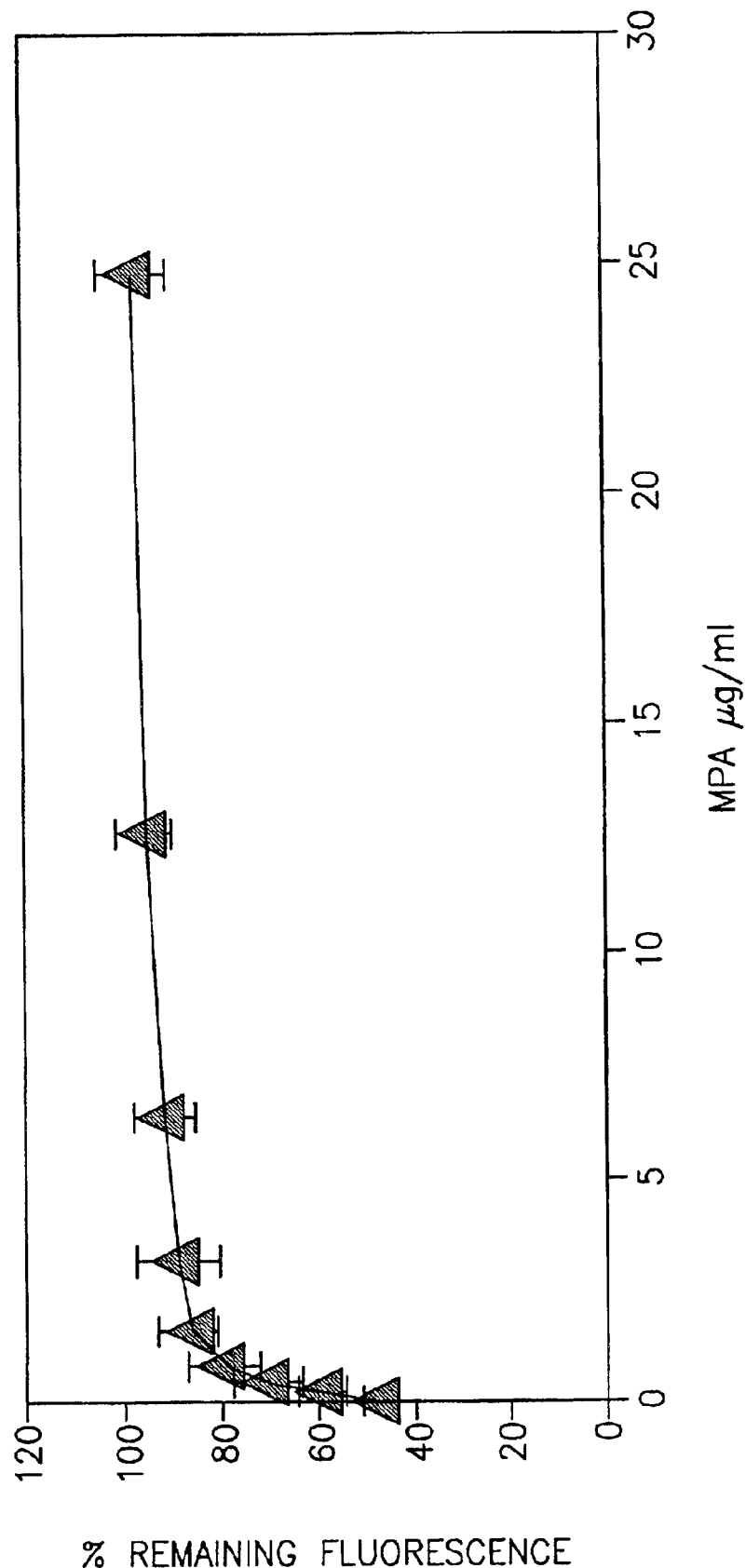

FIG. 5 shows that synthetic lethality imposed by MPA causes retention of the survival plasmid in a dose dependent manner. Cells were maintained in 96 well microplates, hygromycin B was removed and replaced with GATA medium+MPA in serial dilutions starting with 25 microgram/microliter. Microplates were read after two weeks.

Figure 6:
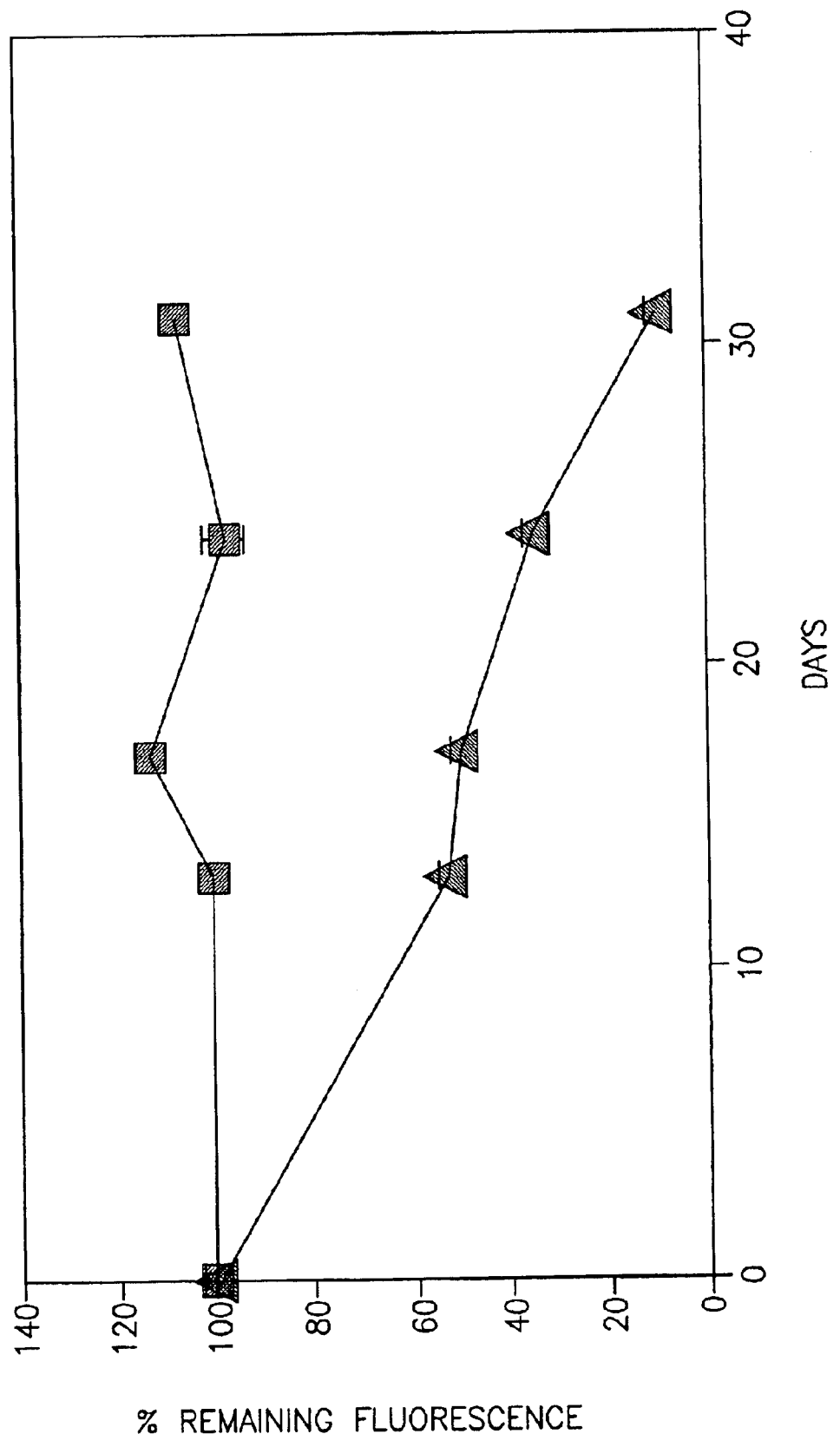

FIG. 6 shows the kinetics of survival plasmid loss or retention under conditions of synthetic lethality imposed by MPA. Cells in 96 well microplates were maintained over the entire time period in either GATA medium+12.5 microgram/ml MPA (rectangles) or in GATA medium alone (triangles).

Figure 7:
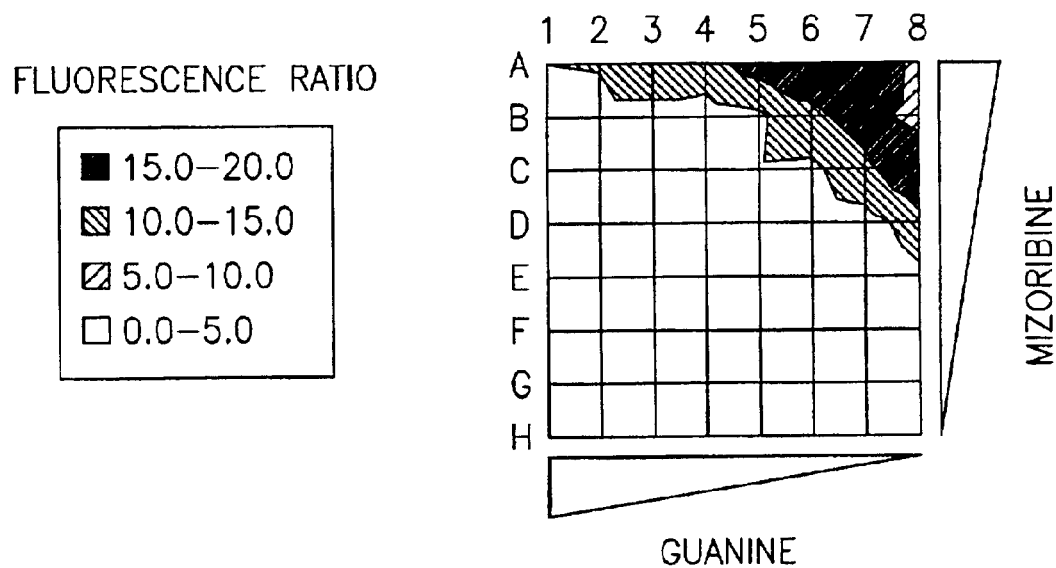

FIG. 7 illustrates chemical synthetic lethality induced by the mizoribine nucleoside analog of IMPDH. Clone 12 cells were grown in microplates in the presence of mizoribine for three weeks. Values of the ribavin. Rows A–H represent the inhibitory drug data.

Figure 8:
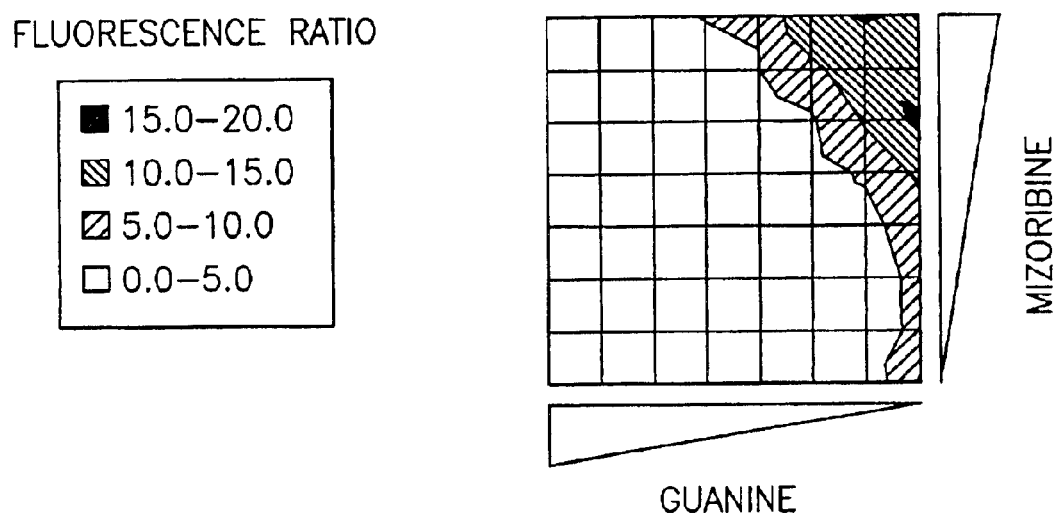

FIG. 8 illustrates chemical synthetic lethality induced by the ribavin nucleoside analog of IMPDH. Clone 12 cells were grown in microplates in the presence of ribavin for three weeks. Values of the flourescence ratio is shown on the left. Rows A–H represent the inhibitory drug data.

Figure 9:
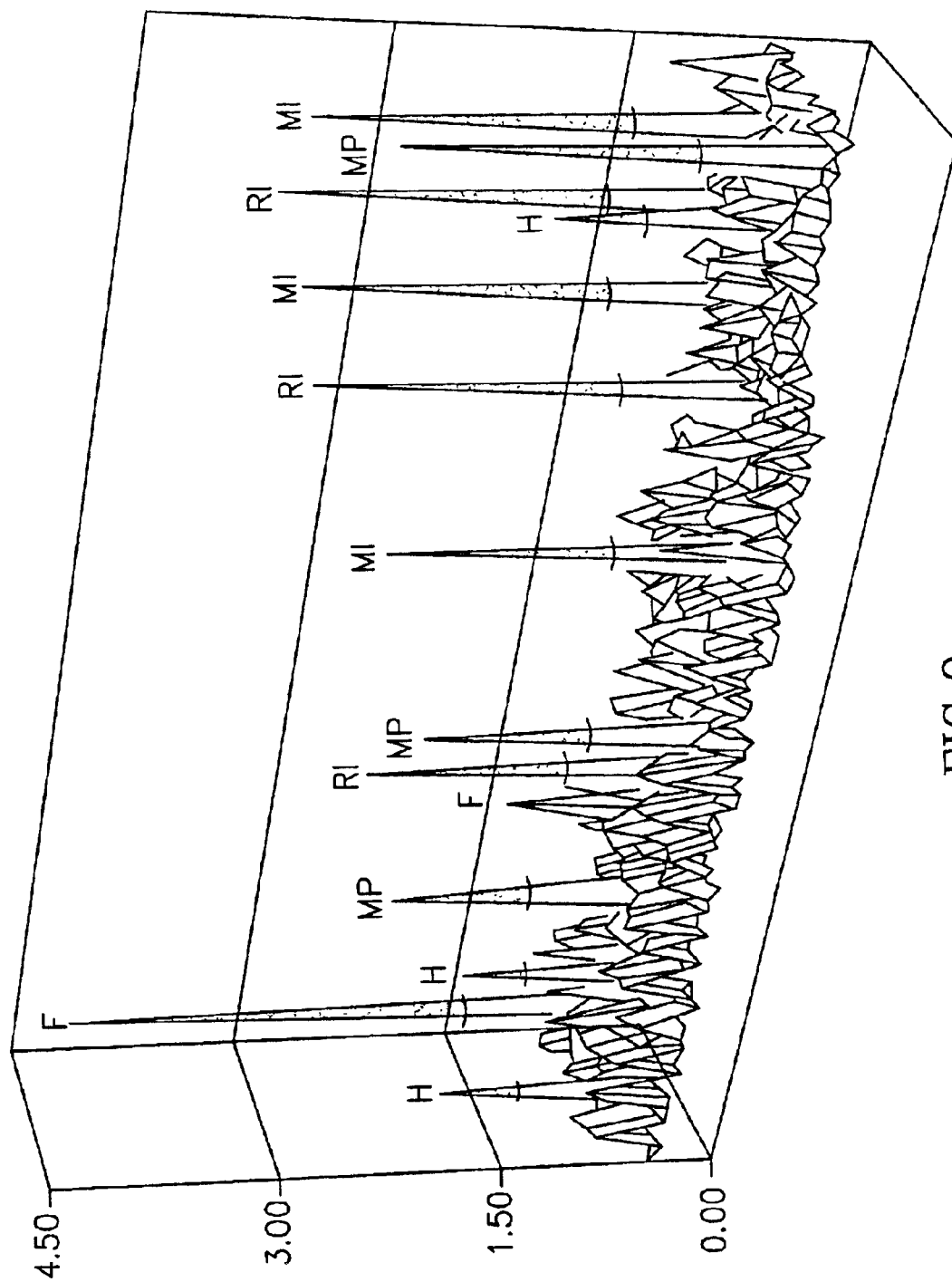

FIG. 9 illustrates detection of chemical synthetic lethality in a blind large-scale test. Clone 12 cells were seeded into 1200 wells. Five chemicals were randomly added: (H)-Hygromycin, (MP)-MPA, RI (ribavin), MI (mizoribine) and alanosine. Flourescence ratio is shown on the left.

Figure 10A:
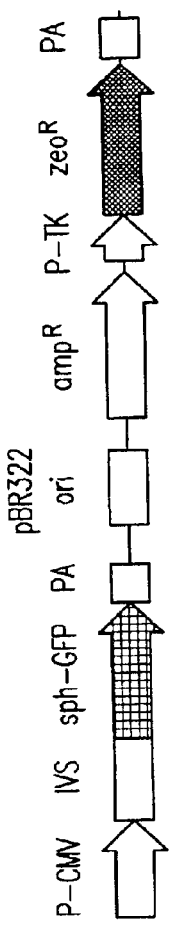
Figure 10B:
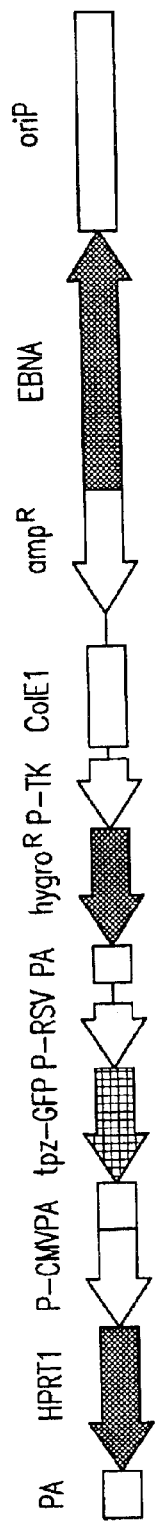

FIG. 10 shows structure of the double-labeled GFP plasmid system and of the library expression vector. (A) The pIS integrating sphGFP vector with a zeo$^R$ dominant selectable marker. (B) The HPRT1-tpzGFP survival plasmid. (C) The truncated sense and antisense cDNA library vector. P-CMV, P-RSV and P-TK indicate the viral promoters of CMV, RSV and herpes TK1, respectively. IVS represents the rabbit globin second intron, while PA stands for polyadenylation signal. The zeo$^R$, hyg$^R$, neo$^R$ and amp$^R$ identify the resistance genes for zeocin, hygromycin B, G418 and ampicillin, respectively.

Figure 11A:
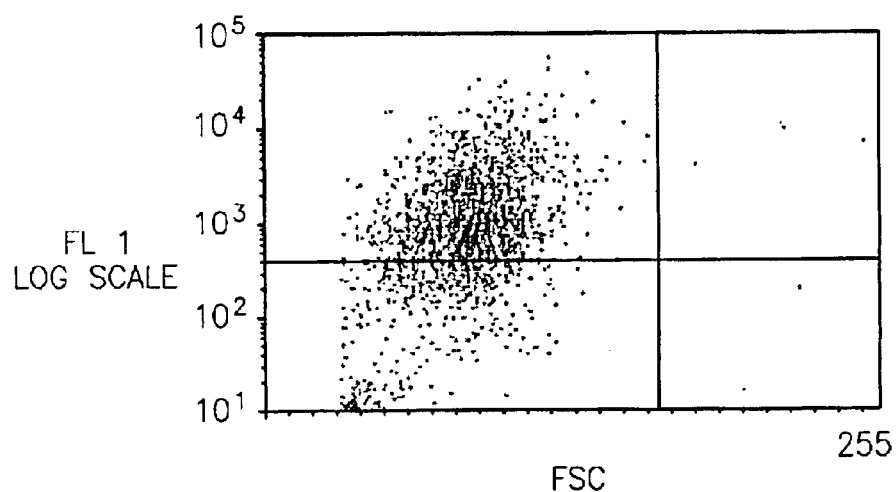
Figure 11B:
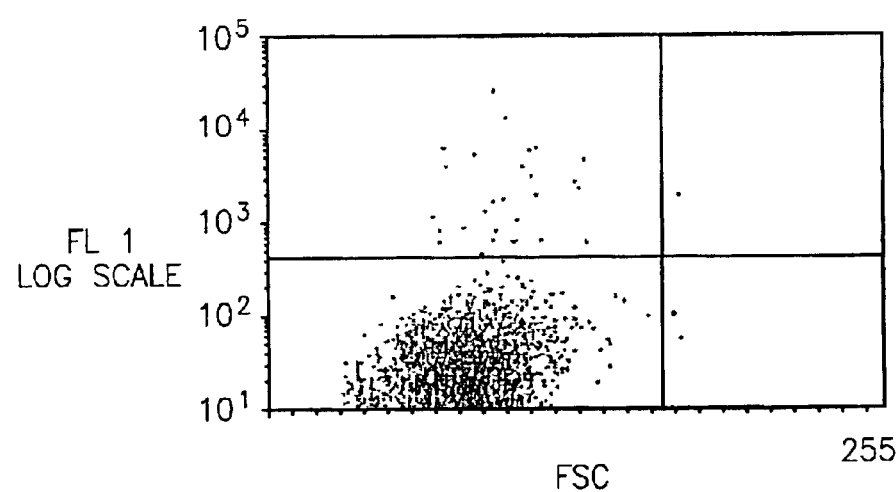

FIG. 11 demonstrates FACS analysis of the retention of tpzGFP-expressing episomal survival plasmid. (A) Clone 13 cells maintained under selection with hygromycin B, the resistance gene that is encoded by the survival plasmid. (B) Clone 13 cells grown without hygromycin B selection for the entire time period. (C) Clone 13 cells transfected with the truncated sense and antisense cDNA library, and grown in the presence of G418 in order to retain the library plasmid. TpzGFP fluorescence is shown on the Y-axis while forward scatter (FSC) is shown on the X-axis.

Figure 12:
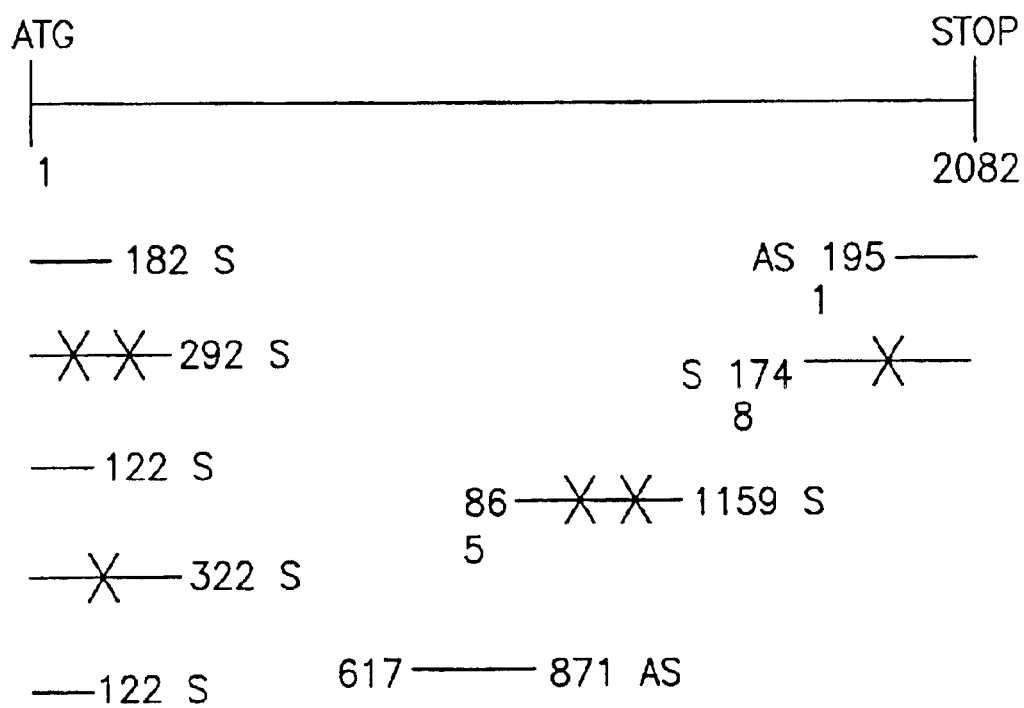

FIG. 12 is a schematic representation showing the localization of the rescued putative GSEs within the GMPS coding region. ATG and STOP symbols indicate the translation initiation and termination codons for the human GMPS cDNA, respectively. The numbers show the base pair position of each fragment within the GMPS cDNA. Sense (S) or antisense (AS) orientation is also shown. X indicates a single base pair substitution from the wild-type sequence.

DETAILED DESCRIPTION OF THE EMBODIMENTS

For convenience, the meaning of certain terms and phrases employed in the specification, examples, and appended claims are provided below:

Non-essential gene—a gene whose function is non-essential to the viability of the cell, either because it is dispensible for cell metabolism or due to the existence of one or more other genes which functionally overlap with it.

Molecule—In the present invention a molecule can be in one embodimenta chemical reagent, in another embodiment a nucleic acid, in another embodiment a drug, in another embodiment a nucleic acid, in another ambodiment ribozymes, in another embodiment RNA aptamers, in another embodiment peptide aptamers.

Drug—the the term drug refers to any molecule (see above) which has a therpeutic efficency, and could serve to treat or to relief a diseased condition.

Non-lethal mutation—a mutation within a non-essential gene or a defect within an essential gene which is partial and thus leaves the cell viable.

Gene of interest—a specific gene which is either non-essential for viability or an essential gene carrying a non-lethal mutation. Its function may be known or unknown. An example without being limited is the hypoxantine-guanine phosphoribosyl transferase enzyme.

Synthetic or synergistic lethality—a lethal cell phenotype which is the result of either the synergistic incapacitation of two genes, or due to the overexpression of one gene on the background of the incapacitation of the gene of interest and vice versa. Either one of these two conditions may also require the overexpression and/or underexpression of other gene(s). The incapacitation of activity may be full or only partial. The incapacitation may be as a result of a resident mutation, or due to an externally inserted element, such as a truncated cDNA, an antisense cDNA molecule or a chemical reagent.

Survival plasmid—a gene vehicle/vector which carries either a functioning copy or a dominant-negative mutant of a gene of interest. The plasmid is not incorporated into the genome of the cell, and yet can autonomously replicate within the cell (i. e. an episome). The episome includes an origin of DNA replication which may be of viral or mammalian origin, and a nuclear antigen gene. The plasmid is spontaneously gradually lost from the cell population.

Genetic suppressor element (GSE)—a nucleic acid capable of suppressing genetic expression in a dominant-negative fashion. Examples of GSEs are antisense cDNA, truncated sense cDNA, DNA encoding RNAi, duplexes of 21-nucleotide RNAs and other forms of synthetic duplex RNAs with overhanging 3' ends. These either encode antisense RNAs, dsRNAs or RNAs having inverted repeats (both belonging to the RNAi type), or constitute synthetic small interfering RNAs (siRNAs), RNA aptamers, ribozymes, peptide aptamers, or truncated polypeptides.

Modulators of gene expression—a group of DNA/RNA/polypeptide molecules which affect gene expression of the host cells. These DNA molecules are either GSEs or over-expressed wild-type genes.

Vector vehicles for modulators of gene expression—a group of vectors containing among others: episomal mammalian expression vectors, retroviral vectors, other RNA-based viral vectors, DNA viral vectors and chimeric transposable element vectors an example without being limited is a chimeric EBV-based pisomal plasmid.

Plurality of molecules can be used interchngeably with a chemical library and/or a genetic library—in one embodiment without limitation it is a group of different Chemical Reagents which may comprise synthetic as well as natural compounds. This definition also includes, but is not limited to, in one embodiment to drug compounds, in another embodiment to synthetic antisense DNA oligonucleotides which may also be modified (phosphorothioate antisense oligodeoxynucleotides, chimeric oligodeoxynucleotides, etc.), in another embodiment to ynthetic small interfering RNAs. In another embodiment it is a genetic library which is a group of vectors containing random DNA fragments from a given species and cloned appropriate hosts.

Gene of interest—refer in this invention to a gene which serve as a basis for screening other genes, chemicals or drugs due to an interaction with the gene.

Reporter gene—the reported genes serve for the determination of the palsmid of the invention. In one embodiment the products of the reporter genes are fluorescent products. An example without limitation is a GFP gene.

Transfection/transfected/transfecting as used herein, the term "transfection" means the introduction of a nucleic acid, e.g., an expression vector or synthetic single or double-stranded DNA/RNA, into a recipient cell by nucleic acid-mediated gene transfer. "Transformation", as used herein, refers to a process in which a cell's genotype is changed as a result of the cellular uptake of exogenous DNA, RNA or peptide.

In one embodiment there is provided a method for screening molecule which have a synthetic lethal property when in combination with a gene of interest carrying a non-lethal mutation for example, without being limited, a gene for HPTR1-hypoxantin-guanine phosphoribosyl tarnsferase, the method comprising the steps of: i. transfecting a first reporter gene which can be for example without limitation a variant GFP gene into a non yeast eukaryotic cell such as mammalian cells having a genome comprising a gene of interest which carries a non-lethal mutation, or a genome which is null for the gene of interest; ii. selecting clones stably expressing the first reporter gene; iii. Introducing into the cells according to the methods described in the Example section a survival plasmid comprising a functioning copy of the gene of interest, a second reporter gene selectable marker, which could be without limitation another variant of GFP gene, an origin of DNA replication and a nuclear antigen gene essential for replication of the plasmid within the cells, wherein the survival plasmid is autonomously replicating and spontaneously lost from the cells; vi. growing the cells under normal conditions which are well known to anyone who is skilled in the art in the presence of a selection compound such as without limitation Hygromycin which selects for the selectable marker; vii.

selecting cell clones stably expressing the second reporter gene and the functioning copy of the gene of interest the selection is performed, without limitation, by a flurescent light microscopy and/or using a fluorescence plate reader ; viii. removing selection for the selectable marker, and adding molecules destined for screening of their ability to impose selective pressure enforcing retention of the unstable survival plasmid. ix. determining survival plasmid retention in cells, according to the method which is well explained in the Examples section and is based on calculation of the ratio of the emission and/or the excitation of the fluorescent products of the reporter gene thus identifying a molecule having a synthetic lethal property when in combination with non-lethal mutated gene of interest.

It should be noted in this respect that the details, the examples and the conditions of each component of the above described embodiment may be applied, without limitation to the other embodiments described below. Further details without being limited may be found in the Examples method.

In this aspect of the invention, molecule such as a chemical reagent for example induced synthetic lethality (i.e. chemical synthetic lethality) identifies biochemical inhibitors or drugs whose lethal effect is dependent on the presence of a whole or partial inactivation of a specific cellular gene (i. e. gene of interest).

In an alternate embodiment of this aspect of the invention, there is provided a method for screening a chemical library comprising a plurality of molecule types in mammalian cells having a genome, in order to identify a molecule type having a gene-specific lethal property in the cell. The cellular gene of interest may be either deficient, or overexpressed in its normal/mutant form. In this specification, expression of the gene of interest includes all of these possibilities.

In another embodiment there is provided a method for screening a cDNA molecule, which has a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. selecting cell clones stably expressing the second reporter gene and the functioning copy of the gene of interest; vi. incorporating the cDNA molecule—into a vector vehicle containing a second selectable marker gene so as to obtain a vector vehicle-cDNA molecule. The vehicle is according to one embodiment an episomal mammalian expression vector vii. transfecting cells with vector vehicles-cDNA molecules while removing selection for the first selectable marker, and instituting selection for pools of cells expressing the second selectable marker gene. viii. determining survival plasmid retention in cells, thus identifying a cDNA having a synthetic lethal property when in combination with non lethal mutated gene of interest.

In a further embodiment of this aspect of the invention, there is provided a method for screening a collection of DNA molecules selected from the group consisting of antisense cDNA, truncated cDNA, DNA encoding RNAi, full-length cDNA, genomic DNA, or any other DNA form in order to identify among them one or more modulators of gene function which are synergistically lethal to a mammalian cell, the cell having a genome which expresses a non-lethal mutant gene of interest.

Cells maintaining the survival plasmid due to expression of a GMPS GSE, exhibit a high tpzGFP expression, allowing their isolation from the total cell population by FACS sorting. Putative GSE-containing episomes were recovered from the low molecular weight DNA fraction. Individual GSE-containing episome clones were retransfected into the recipient cell system, and pools of secondary transfectants displaying a high tpzGFP to sphGFP ratio over time were spotted by periodic readings with a microplate fluorescence reader. Retention of the HPRT1 survival plasmid is dependent on continued selection with G418 for the GSE-expressing episomal vector. As expected from GSEs, irrespective whether their polarity was sense or antisense, they had a dominant-negative effect on the activity of the GMPS endogenous gene. Noteworthy, GSE-containing clones exhibiting as much as 52–73% of the normal GMPS activity were still picked up by our screen (Table2). Similarly, the dose response of IMPDH inhibitors such as mycophenolic acid, mizoribine, and ribavirin, indicate that partial inhibition of IMPDH enzyme activity is accompanied by subsaturated tpzGFP fluorescence levels, reflecting a lower requirment for the survival plasmid encoded HPRT1 enzyme.

As can be seen in the Examples section, using the method described here, one could identify a gene (GMPS) synthetic lethal to a gene of interest (HPRT1). In comparison to the yeast screen (1), this method combines the "mutagenesis" together with the rescue of the synthetic lethal GSEs into a single step. This system allowed isolation of dominant-negative mutants, which should be useful on their own. To the best of our knowledge these mutants are the first dominant-negative suppressors to be described for the GMPS gene.

Initially, the GSE methodology was used to isolate dominant-negative mutants of single given genes, based on the ability of such constructs to disrupt a drug-induced apoptotic response, or to abrogate cell transformation. A further extension to this basic theme has been the use of random libraries of either antisense RNA alone or GSEs for isolation of apoptotic genes via actual selection for survival. Because of the high complexity of random GSE libraries, where each cDNA is usually represented by at least tens of antisense and truncated sense short DNA fragments, enrichment steps for cDNAs of interest have been employed prior to the construction of such libraries. As might have been anticipated, some of the apoptotic genes selected by this approach turned out to be tumor suppressors. The present report demonstrates that incorporation of the GSE method together with a FACS sorting step, into a genetic synthetic lethality screen leads to isolation of dominant-negative mutants for a gene of interest. Clearly, this approach should enable the isolation of new survival/antiapoptotic genes, some of which may turn out to be dominant oncogenes, such as Bcl2, Survivin and others.

To accomplish a genetic synthetic lethality screen at the multi-gene level, the usage of either an enriched cDNA pool, and/or the employment of several rounds of sorting by FACS (in which DNA from GSE containing plasmids is reintroduced, after amplification in bacteria, into recipient cells and subject to decay and selection for fluorescent cells by FACS), is than performed.

Enrichment for human cDNAs, serving as the source for making the GSE library, could be performed by any one of a number of methods, such as subtractive hybridization, differential display, or assaying for gene activity by DNA microarrays. In comparison to a GSE expressed by a retroviral vector present usually as one copy per cell, our method has the advantage of the employment of a multicopy episomal vector, whose GSE activity is not subject to modulation by neighboring chromosomal sequences.

The genetic synthetic lethality screen need not be confined to the use of antisense or truncated cDNAs. Other GSEs such as without limitation libraries of ribozymes, RNA aptamers, peptide aptamers or synthetic small interfering RNAs may be used by applying the same methods.

In another embodiment there is provided a method for screening a drug which has a synthetic lethal property when in combination with a gene of interest carrying a non-lethal mutation, the method comprising the steps of: i. transfecting a first reporter gene into a non-yeast eukaryotic cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, which according to one embodiment is a dominant selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v.

selecting cell clones stably expressing the second reporter gene and the functioning copy of the gene of interest; vi. adding the drug for screening of its ability to impose selective pressure for the retention of the spontaneously lost survival plasmid to the cell clones of step v. vii. determining survival plasmid retention in cells, thus identifying a drug having a synthetic lethal property when in combination with non lethal mutated gene of interest.

In another embodiment there is provided a method for screening a chemical agent which which have a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. adding the chemical agent for screening of its ability to impose selective pressure for the retention of the spontaneously lost survival plasmid to the cell clones of step V. vi. selecting cell clones stably expressing the second reporter gene and the functioning copy of the gene of interest; vii. Determining survival plasmid retention in cells which survive, thus identifying a chemical agent which has a synthetic lethal property when in combination with non lethal mutated gene of interest.

In another embodiment there is provided a method for screening a library comprising a plurality of molecules in order to identify molecule/s having a synthetic lethal property when in combination with a gene of interest carrying a non-lethal mutation, the method comprising the steps of: i. transfecting a first reporter gene into mammalian cells having a genome comprising a gene of interest which carries a non-lethal mutation; ii. selecting clones stably expressing the first reporter gene; iii. introducing into the cells a survival plasmid comprising a functioning copy of the gene of interest, a second reporter gene, a selectable marker, an origin of DNA replication and a nuclear antigen gene essential for replication of the plasmid within the cells, wherein the plasmid is spontaneously lost from the cells; vi. growing the cells in the presence of a selection compound which selects for the selectable marker; v. selecting cell clones stably expressing the second reporter gene and the functioning copy of the gene of interest; vi. adding the library comprising a plurality of molecules for screening of its ability to impose selective pressure for the retention of the spontaneously lost survival plasmid to the cell clones of step V. vii. determining survival plasmid retention in cells, thus identifying a molecule/s within a library having a synthetic lethal property when in combination with non lethal mutated gene of interest.

The invention enables also a method of screening a molecule, or a gene or a drug that are synthetic lethal when in combination mutant or normal gene of interest which is overexpressed as is the situation without limitation with oncogenes such as without being limited RAS.

In another embodiment there is provided a method for screening molecule which have a synthetic lethal property when in combination with a mutant or normal gene of interest which is overexpressed, the method comprising the steps of: i. transfecting a first reporter gene into mammalian cells having a genome comprising a mutant or normal gene of interest which is overexpressed, ii. selecting clones stably expressing the first reporter gene; iii.

introducing into the cells a survival plasmid comprising a dominant-negative mutant of the gene of interest, a second reporter gene, selectable marker, an origin of DNA replication and a nuclear antigen gene essential for replication of the plasmid within the cells, wherein the survivsal plasmid is autonomously replicating and spontaneously lost from the cells; vi.

growing the cells in the presence of a selection compound which selects for the selectable marker; vii. selecting cell clones stably expressing the second reporter gene and the dominant-negative mutant of the gene of interest; viii. removing selection for the selectable marker, and adding molecules destined for screening of their ability to impose selective pressure enforcing retention of the unstable survival plasmid. ix. determining survival plasmid retention in cells, thus identifying a molecule having a synthetic lethal property when in combination with the a mutant or normal gene of interest which is overexpressed.

In another embodiment there is provided a method for screening a cDNA molecule, which have a synthetic lethal property when in combination with a mutant or normal gene of interest which is overexpressed, the method comprising the steps of: i. transfecting a first reporter gene into a mammalian cells having a genome comprising a mutant or normal gene of interest which is overexpressed; ii. selecting clones stably expressing the first reporter gene;

iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the plasmid is spontaneously lost from the cells; iv. growing the cells in the presence of a selection compound which selects for the selectable marker; v. selecting cell clones stably expressing the second reporter gene and the dominant-negative mutant of the gene of interest; vi.

incorporating the cDNA molecule—into a vector vehicle containing a second selectable marker gene so as to obtain a vector vehicle-cDNA molecule. vii. transfecting cells with vector vehicles-cDNAs molecules while removing selection for the first selectable marker, and instituting selection for pools of cells expressing the second selectable marker gene. viii.

determining survival plasmid retention in cells, thus identifying a cDNA having a synthetic lethal property when in combination with the a mutant or normal gene of interest which is overexpressed.

In another embodiment there is provided a method for screening a drug which have a synthetic lethal property when in combination with a mutant or normal gene of interest which is overexpressed, the method comprising the steps of: i. transfecting a first reporter gene into a non-yeast eukaryotic cells having a genome comprising a mutant or normal gene of interest which is overexpressed; ii. selecting clones stably expressing the first reporter gene; iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the survival plasmid is spontaneously lost from the cells; iv. growing the cells in the presence of a selection compound which selects for the selectable marker; v. selecting cell clones stably expressing the second reporter gene and the dominant-negative mutant of the gene of interest; vi. adding the drugs destined for screening their ability to impose selective pressure enforcing retention of the spontaneously lost survival plasmid; vii. determining survival plasmid retention in cells, thus identifying a drug having a a synthetic lethal property when in combination with the mutant or normal gene of interest which is overexpressed.

In another embodiment there is provided a method for screening a library comprising a plurality of molecules which have a synthetic lethal property when in combination with a mutant or normal gene of interest which is overexpressed, the method comprising the steps of: i. transfecting a first reporter gene into mammalian cells having a genome comprising a mutant or normal gene of interest which is overexpressed; ii. selecting clones stably expressing the first reporter gene; iii. introducing into the cells a survival plasmid comprising a dominant-negative mutant of the gene of interest, a second reporter gene, a selectable marker, an origin of DNA replication and a nuclear antigen gene essential for replication of the plasmid within the cells, wherein the plasmid is spontaneously lost from the cells; vi. growing the cells in the presence of a selection compound which selects for the selectable marker; v. selecting cell clones stably expressing the second reporter gene and the dominant-negative mutant of the gene of interest; vi. adding the library comprising a plurality of molecules in order to identify those that impose selective pressure enforcing the retention of the spontaneously lost survival plasmid. vii. determining survival plasmid retention in cells, thus identifying at least one molecule within a library having a synthetic lethal property when in combination with the mutant or normal gene of interest which is overexpressed.

In another embodiment there is provided a kit for screening a library containing a plurality of molecule types in mammalian cells having a genome, in order to identify a the molecule having a gene-specific lethal property in the cell, comprising: an integration plasmid comprising a first reporter gene; a survival plasmid compatible with a mammalian cell comprising a functional copy of a gene of interest or a dominant-negative mutant of a gene of interest, a reporter gene, a dominant selectable marker gene, an origin of DNA replication and a nuclear antigen essential for replication of the survival plasmid, the survival plasmid being spontaneously lost from the cell.

In another embodiment there is provided a kit for screening a group of DNA molecules in order to identify among them one or more modulators of gene expression which are synergistically lethal to a mammalian cell together with a gene of interest, comprising: an integration plasmid comprising a first reporter gene; a survival plasmid compatible with a mammalian cell comprising a functional copy of a gene of interest or a dominant-negative mutant of a gene of interest, a reporter gene, a dominant selectable marker gene, an origin of DNA replication and a nuclear antigen gene essential for replication of the survival plasmid, the survival plasmid being spontaneously lost from the cell; and a vector vehicle containing a second dominant selectable marker gene and carrying either a human GSE library or a wild-type cDNA library.

In another embodiment there is provided a survival plasmid compatible with a mammalian cell comprising a functional copy of a gene of interest, a reporter gene, a dominant selectable marker gene, an origin of DNA replication and a nuclear antigen essential for replication of the episome, the episome being spontaneously lost from the cell, wherein the product of the reporter gene is a mutant green fluorescent protein (GFP).

In another embodiment there is provided a survival plasmid compatible with a mammalian cell comprising a dominant-negative mutant of a gene of interest, a reporter gene, a dominant selectable marker gene, an origin of DNA replication, and a nuclear antigen gene essential for replication of the episome, the episome being spontaneously lost from the cell, wherein the product of the reporter gene is a mutant green fluorescent protein (GFP).

In this aspect of the invention, synthetic lethality imposed by either a GSE or by an overexpressed full-length cDNA identifies a gene function or functional links between genes.

The method of the invention differs from the synthetic lethality screen previously described in yeast in the following respects:

(1) Synthetic lethality as disclosed in yeast is recognized by the visible color of yeast colonies grown on agar within petri dishes. The majority of colonies exhibit the appearance of white sectors within red colonies, while a synthetic lethal condition prevents the appearance of white sectors in a primarily red colony. The accumulation of red pigment is enabled by the reporter gene acting together with other genes. In contrast, the method of the invention involves the seeding of human/mammalian cells into microtiter plates, and the periodic measurement in a fluorescent plate reader of the double-label fluorescent ratio of two fluorescent proteins. Retention over time of a high ratio in the readings of a fluorescent variant encoded by the survival plasmid to a second fluorescent variant produced from a chromosomally integrated gene, indicates selection for maintenance of the survival plasmid and thus a synthetic lethality condition. The fluorescence is a direct product of the reporter gene. (2) Synthetic lethality is imposed in yeast by randomly mutagenizing the whole yeast genome with a chemical mutagen, thus leading to random gene inactivation. In contrast, in the present invention, synthetic lethality is achieved by either a chemical inhibitor (chemical synthetic lethality) or a genetic incapacitation via a full-length cDNA/ GSE (genetic synthetic lethality). The latter involves overexpressing full-length sense cDNA libraries or GSE libraries, either one of which is incorporated into episomal plasmids, retroviral vectors, other RNA-or DNA-viral vectors, or chimeric transposable elements. Identification of the gene which is synthetic lethal with the gene of interest is performed in yeast by first isolating those colonies in which the red pigment was maintained and no white sectors appear. Those colonies putatively harbor a chromosomally mutated gene which is synthetic lethal with the gene of interest. Those yeast colonies are transfected by a normal yeast genomic library incorporated into a yeast multi-copy plasmid. Those transformants transfected by and expressing a wild-type copy of the chromosomally mutated gene, no longer sustain a synthetic lethality condition, and therefore no longer need to retain the survival plasmid. Those few colonies are recognized by the appearance of white sectors, from which the plasmid DNA is extracted, transformed into bacteria and further analyzed for the identity of the yeast gene insert by standard recombinant DNA methods.

Identification of the genetic element which confers the synthetic lethal phenotype in human/mammalian cells of the present invention, on the other hand, does not require a further transfection with a normal gene library. This is because, unlike in the yeast method, gene incapacitation is not achieved by mutagenizing the endogenous resident cell genome but rather by an exogenous DNA element working either in a dominant-negative fashion or by overexpression of a wild-type cDNA. Accordingly, the external genetic element conferring the synthetic lethality is recovered by either one of two approaches, depending on the type of vector/vehicle used: (a) an episomal plasmid, chimeric RNA or DNA based viral replicons are rescued by Hirt supernatant-extract mediated bacterial transformation or purification of packaged virus-like particles, respectively; (b) chromosomally integrated GSE or a wild-type sense cDNA library incorporated into either a retroviral vector or a chimeric transposable element, are recovered by PCR on genomic DNA.

The availability of a large number of mutant human cell lines derived from genetic disorders on the one hand, and the ability to employ homologous recombination for gene disruption in somatic human cells on the other, constitutes a large reservoir of recipient cells and genes of interest.

The cells which may be used in the method of the invention are mammalian cells. Preferably they are human cells, but the same principle may be applied to e. g., rodent cells harboring a survival plasmid with the appropriate replication properties.

The survival plasmid contains a reporter gene so as to enable determination of the presence of the plasmid in the cells. The product of the reporter gene may be any detectable molecule, such as the following biosensors: luciferin (luciferase substrate); aequorin; Fluo-3/acetoxymethyl (esterase substrate); FDG (3-gal substrate); or CCF2 which is a p-lactamase substrate [J. E. Gonz lez and P. A. Negulescu, Curr. Opin. Biotechnol. 9,624 (1998)]. Preferably, the reporter gene encodes a fluorescent protein whose expression can be distinguished from that of a second fluorescent protein marking the cell number. Non overlapping excitation or emission spectra of the two fluorescent proteins allows for double-label fluorescence measurement.

Accordingly the cells are also made to incorporate in their genome a second reporter gene which indicates the number of cells. By comparing the signals obtained from the two reporter genes, a relative ratio between the number of survival plasmids and the number of cells may be determined.

The methods of the invention may be carried out using conventional systems for growing, scanning and sorting cells, such as microtiter plates, 96well. 384-well or other high-density microplates, a microplate fluorescent reader, and a fluorescent activated cell sorter (FACS). The methods are especially useful in high throughput screening, where automation allows for the rapid screening of large number of chemicals as well as the full spectrum of mammalian genes and their respective GSEs.

The present invention may be used in a number of applications:

The first aspect of the invention should prove advantageous in the search of drugs which synergize with particular gene deficiencies or gene status to cause cell lethality as well as identifying drug compounds having gene-specific lethal properties. A special application of this aspect would be to look for chemicals which kill either a benign or cancerous cell growth in a defined genetic milieu where the chemical is synthetic lethal with a particular gene, either in a deficient form (present in tumor suppressor genes) or overexpressed normal/mutated form (present in oncogenes).

The second aspect of the invention is useful in identifying human genes whose under or over-expression causes lethality of human cell lines with defined genetic abnormalities, be it either gene deficiency or overexpression of the normal/ mutated gene form. Such genes are obviously potential targets for drugs aimed at eliminating the affected cells/ tissue. The application of this approach to human tumor-derived cell lines, is particularly amenable to identification of targets for cancer therapy.

Above and beyond the identification of gene targets of therapeutic interest in defined genetic background, the invention should prove useful as a tool for basic research. In particular, the invention may enable researchers to rapidly screen large sets of gene products for functional interactions and helps define genetic pathways within the cell (2).

The method using rodent cells should be useful as a model for human genetic traits and responses in drug development and disease research. For example, mutant mice generated by either ectopic overexpression, homologous recombination or tagged random mutagenesis, supply a large source of recipient mutated mouse embryo fibroblasts which, together with the methods of the invention, will greatly facilitate research and development of new drugs and therapeutic strategies for human beings.

Also included in the invention are kits for synthetic lethality screening. One such kit in accordance with the first aspect of the invention would preferably include an episomal survival plasmid and an integrating vector, each carrying a reporter gene, for a chemical synthetic lethality screen. A kit in accordance with the second aspect of the invention would preferably include the above genetic elements together with a library of GSEs or sense cDNAs incorporated within an extrachromosomal vector.

The present invention describes the development and the feasibility of a genetic synthetic lethality screen in cultured human cells. The methodology is an extension of the chemical synthetic lethality screen, which was disclosed in U.S. patent application Ser. No. 09/931,444 . The invention shows that the chemicals used in the chemical screen can be replaced also by dominant-negative GSEs. Thus, the methods described herein is a general screening method which can apply to drugs, cDNA, different chemical compounds as well as plurality of molecules.

Because the method is based on identification of a lethal phenotype, it is particularly relevant to the search for human genes acting in the same essential pathway, or along two parallel ones. Therefore, such genetic synthetic lethality screens should have a major impact on human functional genomics. Moreover, the genetic synthetic lethality screen, when applied to human tumor cell lines having known primary genetic alterations, could lead to identification of new, perhaps even unexpected, secondary targets for cancer therapy. As targets identified by this approach would result in cellular synthetic lethality only when the primary tumor alteration is present, a high selectivity towards the tumor is insured.

EXAMPLES

Chemical Synthetic Lethality Screening
Experimental Procedures

A. Construction of Plasmids

The plasmid pIS was constructed by replacing the BamHl fragment encoding CD20 from pCMV-CD20 (kind gift from S. van den Heuvel and E. Harlow) with a blunt-ended HindIII-BamHI fragment containing the coding sequence of sphGFP from the pGFPsph-b [R] vector (Packard Instruments).

The episomal HGPRT-tpzGFP survival plasmid was constructed by first cloning a HindIII-BamHI blunt-ended fragment encoding the tpzGFP and polyadenylation signal from the pGFPtpz-b [R] vector (Packard Instruments) into the HindIII site of pCEP4 (Invitrogen). The coding sequence of HGPRT was cloned into pcDNA3 (Invitrogen) and subsequently removed together with the CMV promoter by digestion with Bglll and BamHl. This fragment was then cloned into the BamHI site of the pCEP4-GFP vector. The final survival plasmid was produced by cloning the KpnI-BamHI fragment of the pCEP4-HGPRT-tpzGFP vector into the Kpnl BamHl site of pREP4 (Invitrogen), such that tpzGFP is under the influence of the RSV promoter.

B. Expression of Constructs in Cells

HGPRT-deficient HT1080 fibrosarcoma cells (W. F. Benedict, et al., Cancer Res. 44,3471 (1984)) were maintained in Dulbecco's modified Eagle medium (DMEM) supplemented with 10% fetal calf serum (FCS) and 4 mM L-glutamine. This cell line has a generation time of about 24 hours, and a pseudo diploid chromosomal karyotype. Transfections were carried out using the calcium phosphate precipitation technique as previously described (T. Teitz et al., Proc. Natl. Acad. Sci. USA 84,8801 (1987)). For pIS, selection in G418 (Calbiochem) was carried out at 400 microg/ml, while maintenance was at 50 microg/ml. For the HGPRT-tpzGFP survival plasmid, selection in hygromycin B (Sigma) was at 150 microg/ml while maintenance was at 50 microg/ml. Selection and maintenance of the survival plasmid was also carried out in HAT medium (100 microM hypoxanthine, 0.4 microM aminopterin, 16 microM thymidine; Littlefield, J. W. Science 145,709 (1964)). GATA medium was DMEM with 10% dialyzed FCS, plus 3.5 microM guanine-HCI, 0.4 microM aminopterin, 16 microM thymidine and 35 microM adenine.

HATA medium was HAT medium plus 60 microM adenine. Concentrations of adenine were detenined empirically by plating Clone 12 cells into 96 well microplates in either HAT or GAT medium with varying concentrations of adenine. Loss of survival plasmid was followed on a microplate fluorescence reader and the concentration that was not toxic and allowed a rate of plasmid loss similar to spontaneous rates was chosen.

C. Fluorescent Scanning of Microtiter Plates

For fluorescent scanning, cells were trypsinized and distributed at 30,000 cells/well into 96 well microplates (TPP). Growth medium was changed twice a week and plates were grown for up to 75 days. Although cell populations were very dynamic due to shedding of large clumps, almost all wells contained viable, growing cells for the entire span of the experiment. Plates were prepared for scanning by replacement of medium in wells with Hank's balanced salt solution without phenol red. This procedure minimized background fluorescence from the growth medium while maintaining maximal viability. Plates were scanned with an FL600 microplate fluorescence reader using the KC4 software (Biotek Instruments). Excitation for sphGFP was at 380 nin with a bandpass of 20 nm, while emission was measured at 508 nm with a bandpass of 40 nm.

Excitation of tpzGFP was at 495 nm with a bandpass of 20 mn, while emission was measured at 535 nm with a bandpass of 40 nm. To avoid possible artifacts, all wells within a given experiment were assayed for the fluorescence of the two GFP mutants using fixed sensitivities. Integrated sphGFP was used as an internal control for the number of cells. This was achieved by dividing the relative fluorescence resulting from the episomal tpzGFP vector by the relative fluorescence for sphGFP for each well. This ratio was then divided by the average fluorescence ratio for cells maintained under hygromycin B or HAT selection, resulting in a value representing percent remaining fluorescence for each well as compared to wells maintained under continuous selection. The data points are an average for all wells and the calculated standard deviation. Cells were returned to growth medium immediately following scanning.

I. Establishment of a Model System

In order to develop a synthetic lethality screening method in human cells, Epstein-Barr virus (EBV) based episomal vectors, which can replicate autonomously as a low copy number episome in human cells of diverse tissues. were selected as the basis for the survival plasmid (J. L. Yates, N. Warren and B. Sugden, Nature 313,812 (1985); U.S. Pat. No. 4,686,186, whose contents are incorporated herein). However, this vector is an imperfect episome because its retention in human cells requires continued selection for a dominant selectable marker gene built into the vector (D. Reisman, J. Yates and B. Sugden, Mol. Cell. Biol. 5,1822 (1985). M. P. Calos, Trends Genetics 12.463 (1996). N. Dafni and D. Canaani, unpublished results). In the design of the system for human cells, advantage was taken of this spontaneous gradual plasmid loss, by creating synthetic lethal conditions under which retention of the episomal plasmid is essential for viability.

Figure 1:
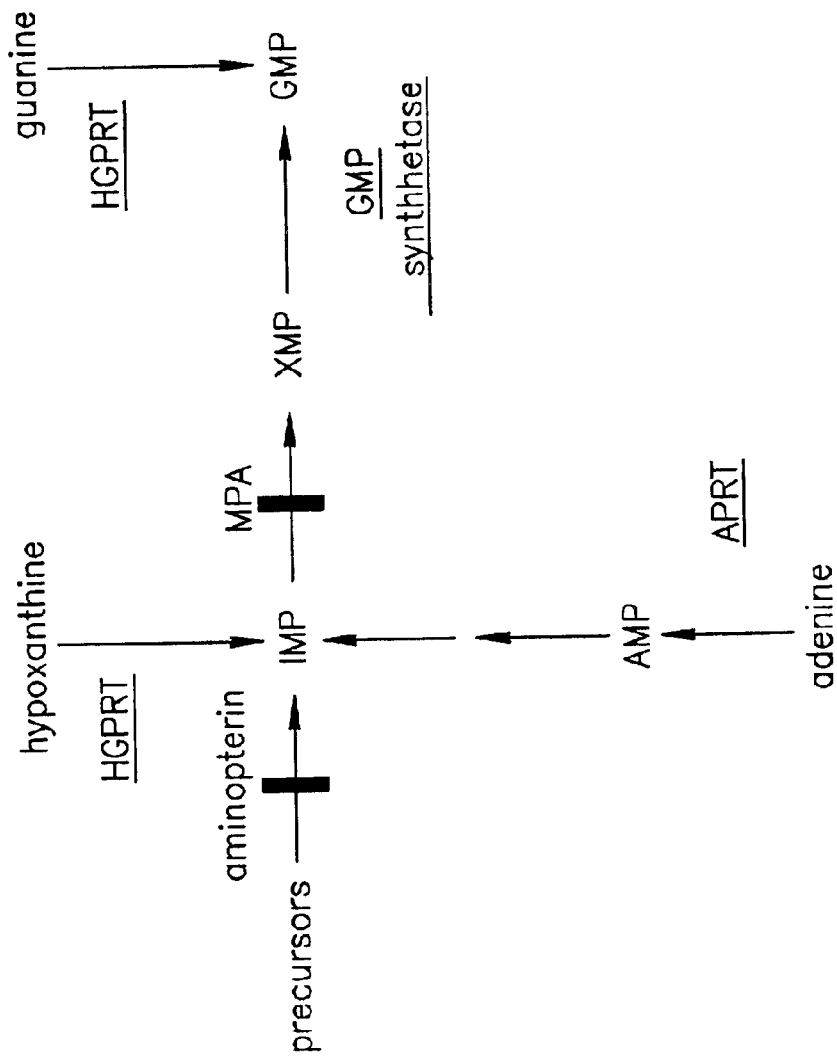
FIG. 1 illustrates de novo and salvage pathways of purine biosynthesis.

As a model system for the establishment of the method, the biosynthetic pathway leading to the production of guanosine monophosphate (GMP) was chosen (FIG. 1). This pathway has been thoroughly studied biochemically and is particularly amenable to a synthetic lethality screen. First of all, the gene of interest in the model system, hypoxanthine-guanine phosphoribosyltransferase (HGPRT), is non-essential for cell survival, since it works in salvage pathways by converting hypoxanthine and guanine to IMP and GMP, respectively. Secondly, immortalized HGPRT-deficient human cell lines are available. Also, a major advantage of this model system is that de novo GMP synthesis can be specifically blocked by certain chemical reagents (FIG. 1). Accordingly, the HGPRT deficient human cells should become dependent on the HGPRT expressing "survival plasmid", when the de novo pathway is blocked by aminopterin or mycophenolic acid (MPA), in the presence of the HGPRT precursors hypoxanthine and guanine, respectively.

II. Stable Transfection of an Internal Control Fluorescent Marker.

Figure 2A:
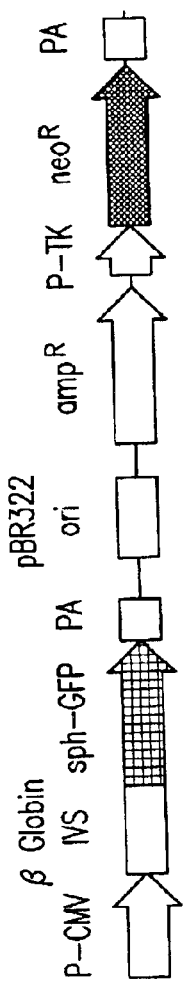

In order to establish synthetic lethality as a high throughput screening system based on fluorescent readout, it is essential to have an internal fluorescent reporter which normalizes the fluorescent reading from the episomal survival plasmid, relative to cell number. To this end, the sapphire-blue green fluorescent protein (sphGFP), a mutant form of the natural GFP from the jellyfish *Aequara victoria*, was chosen (U.S. Pat. No. 5,625,048, the contents of which are incorporated herein). The sphGFP coding region was cloned into a transcription unit driven by the strong CMV immediate-early promoter (U.S. Pat. No. 5,168,062, the contents of which are incorporated herein), and situated upstream of a neoR transcription unit, thus creating the vector pIS (FIG. 2a). As a recipient cell line the HGPRT-deficient variant of the HT1080 fibrosarcoma cell line was chosen (W. F. Benedict, B. E. Weissman, C. Mark and E. J. Stanbridge, Cancer Res. 44, 3471 (1984).

The pIS vector was transfected into these cells, stable clones were selected in G418, and examined with a fluorescent microscope. Clones with >99% fluorescing cells were chosen for further examination (FIG. 3). These were seeded into 96-well microplates, and scanned for fluorescence intensity using a microplate fluorescent reader, as described in the Methods section. Compare to the recipient cells, or medium alone, up to 38-fold fluorescence enhancement was recorded for the sphGFP transformants (data not shown).

As expected, in the linear range of sphGFP reading, a close correlation was seen between the number of cells and the fluorescent intensity. The fluorescent intensity of these cells did not vary appreciably when removed from continuous G418 selection. Thus, the fluorescence levels obtained from the stably integrated sphGFP mutant gene are appreciable and can be easily detected as a mass population by a fluorescent microplate reader.

III. Generation of Stable Transfectants Harboring the Episomal Survival Plasmid

Survival plasmids containing a transcription unit for the human HGPRT cDNA (gene of interest) and a second GFP mutant gene, were constructed onto the backbone of the EBV-based pCEP4/pREP4 episomal vectors (FIG. 2b), as described in the Methods section. These vectors replicate autonomously as episomes in human cells due to the EBV-oriP and EBNA-1 elements (J. L. Yates, N. Warren and B. Sugden, Nature 313,812 (1985)).

They also contain the hygromycin phosphotransferase dominant selectable marker. the bacterial colE1 origin of DNA replication and the (beta lactamase gene).

Figure 2B:
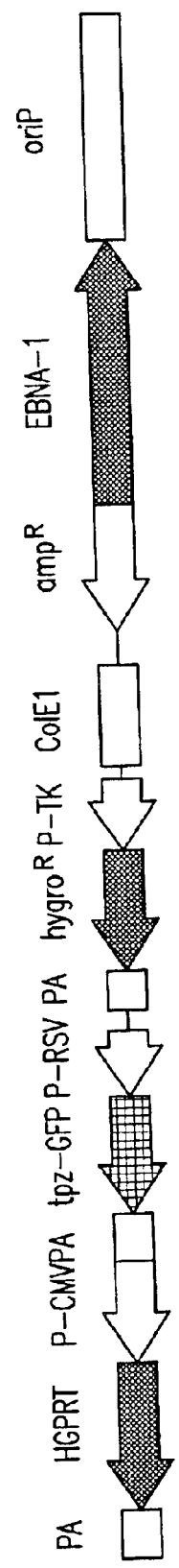

In order to identify the survival plasmid, a second GFP variant was incorporated, the topaz-green GFP mutant gene (tpzGFP), whose expression can be distinguished from the sphGFP mutant. TpzGFP has an excitation peak (514 nm) which does not overlap with that of sphGFP (395 nm), allowing for double-label fluorescence measurements. The corresponding emission peaks are 527 nm for tpzGFP and 511 nm for sphGFP. TpzGFP was cloned under the influence of the RSV promoter (FIG. 2b). The human HGPRT cDNA was inserted in between the unique restriction sites HindIII and BamHI, so that it can be easily replaced by any human cDNA of interest (FIG. 2b). This construct. a HGPRT-tpzGFP survival plasmid, was introduced into one cell clone, HIS4, which displayed stable expression of the integrated sphGFP reporter. Stable clones resistant to hygromycin B were selected for further study, as described in the Methods section.

Most hygromycin B resistant clones were also resistant to HAT medium, indicating expression of the HGPRT transcription unit. Scanning by fluorescence microscopy was used to select several clones that express the tpzGFP in >99% of their cells. The fluorescence resulting from these two GFP variant, one stably integrated into the genome (sphGFP) and one episomal (tpzGFP), could be distinguished by use of two different filter blocks (FIG. 3. D and G vs. E and H). Similar numbers of these cells were then plated into 96 well microplates and scanned by a fluorescent microplate reader. This scanning revealed up to a 140-fold tpzGFP fluorescence increase over HIS4 autofluorescence (data not shown). It can therefore be concluded that the double-label fluorescence from the sphGFP and tpzGFP can be readily distinguished at both the single cell level by fluorescence microscopy, as well as at the mass culture level when grown in microplates, by a fluorescence microplate reader.

IV. Spontaneous Loss of the Survival Plasmid

It was next determined whether spontaneous loss of the survival plasmid could be detected by fluorescence measurements. It was imperative to show that in microtiter plates the expected plasmid loss occurs and could be detected. This is because an inherent feature of the proposed high throughput method is that scanning for genes or chemical reagents, that are synthetically lethal with a human gene of interest, will be performed on cell clones grown in microplate wells. The dynamics of cell division, and therefore the rate of the survival plasmid loss, could be very different in cells grown for long periods in microplates, as opposed to cells stimulated to divide by a regimen of periodic trypsinization, dilution and reseeding. Accordingly, measurement of fluorescence after removal of drug selection was carried out in cells continuously passaged in 90 mm plates as well as in cells grown in microtiter plates. Results from one isolate, Clone 12, carrying an integrated sphGFP gene and an episome-encoded tpzGFP are shown in FIG. 4. Following removal of hygromycin B from the medium, the tpzGFP and sphGFP fluorescence ratios were monitored over time. The calculated ratio was normalized to readings taken at the same time point from cells kept continuously under hygromycin B selection. As shown in FIG. 4, fluorescence from the survival plasmid marked with tpzGFP decayed rather quickly, so that after about one month, Clone 12 lost 80–90% of its initial fluorescence. Importantly, no significant difference in the rate of fluorescence decay could be detected between the cells maintained in microplate wells as opposed to those maintained by continuous passaging in petri dishes (FIG. 4). Assuming that one of the major factors affecting EBV-based plasmid loss is the rate of cell division, it could be that besides the multilayer growth of these transformed cells, the cell shedding which was observed in the microplate wells may also contribute to the dynamics of cell division.

To test whether the gradual loss of tpzGFP fluorescence over time indeed reflects the loss of survival plasmid, two assays were conducted. In one, low molecular weight DNA present in Hirt supernatants (B. Hirt, J. Mol. Biol. 26,365 (1967) of Clone 12 cells was collected at various times after removal from hygromycin B selection. This DNA was used for bacterial transformation. It was found that the decrease of AmpR colonies correlated well with the loss of tpzGFP fluorescence over time (Table 1). In the second assay, a plasmid segregation assay (D. Reisman, J. Yates and B. Sugden, Mol. Cell. Biol. 5,1822 (1985) was carried out. At each time point after drug removal, cells were reseeded into petri dishes containing hygromycin B. It was found that the number of colonies able to grow in the presence of hygromycin B, did indeed decrease at later time points (data not shown).

TABLE 1

Monitoring of spontaneous survival plasmid loss by Hirt supernatant mediated bacterial transformation.
Clone 12 cells were plated at the beginning of the experiment in DMEM without hygromycin B. Cells were continuously passaged throughout the entire experiment. Low-molecular weight DNA present in Hirt supernatants was collected at the indicated time points. All Hirt supernatants were normalized by addition of 1 ng of a chloramphenicol-resistant plasmid prior to the beginning of cell extraction. Each Hirt supernatant transformation of bacteria was plated both on chloramphenicol and ampicillin plates. Values in table were normalized to the number of colonies counted on the chloramphenicol plates.

| Days without selection | Bacterial transformants Per $10^6$ Clone 12 cells | Plasmid loss (k) per day (%) |
|---|---|---|
| 0 | 628 | |
| 21 | 38 | 13.4 |
| 25 | 23 | 13.2 |
| 38 | 16 | 9.7 |
| 46 | 0 | |

*Calculated according to 2.303 log (N0/N) = kT, where N0 = % AmpR colonies at time zero (100%), N = % AmpR colonies remaining after propagation for T days without hygromycin B selection and k = % loss of plasmid per day.

V. Detection of Chemical Reagent Induced Synthetic Lethality

These results demonstrated that, in the absence of selection, the HGPRT-tpzGFP survival plasmid is unstable in HGPRT-deficient HT1080 cells. Its loss or retention can be determined by measuring its normalized fluorescence in a microplate reader. It was then necessary to test whether these features would enable the tracing of a synthetic lethality condition. The biosynthesis of GMP from IMP via XMP can be efficiently blocked using MPA, which inhibits IMP dehydrogenase (FIG. 1). Under these conditions, normal HGPRT-positive cells can use supplied guanine to produce GMP via the salvage pathway, and survive, while HGPRT-deficient cells die. Clone 12. as an inherently HGPRT-deficient cell line, must retain the HGPRT-tpzGFP survival plasmid in order to remain alive in this synthetic lethality situation. Indeed, when hygromycin B was removed from Clone 12 cells grown in GATA medium (medium supplemented with guanine, aminopterin, thymidine and adenine-see Methods section), spontaneous loss over time of the survival plasmid occurred, as traced by a decrease in tpzGFP fluorescence (FIG. 6). It has been shown that under the specific conditions used, this loss is enabled due to a relative surplus of adenine, which besides serving as a precursor for AMP biosynthesis, allows GMP to be synthesized via the AMP-IMP-XMP pathway (data not shown, and see also Methods and FIG. 1).

In contrast, addition of MPA to the GATA medium at successively higher concentrations, caused increasing retention of the survival plasmid, which could be detected by an increase in tpzGFP to sphGFP fluorescence ratio. A dose response was observed which reached a plateau at fluorescence levels similar to those obtained when HAT selection is imposed (FIG. 5). Moreover, as shown in FIG. 6, when fluorescence was observed over time, MPA could cause retention of the survival plasmid for the entire time period, while cells without MPA continued to lose tpzGFP fluorescence. Importantly, almost identical patterns of decay or retention in the presence of MPA were found when cells were grown in medium plus 3 microM guanine, without aminopterin or adenine (data not shown).

IMP dehydrogenase (IMPDH) has two isoforms and is considered to be the rate-limiting enzyme in guanine nucleotide biosynthesis. Two basic types of drugs can effectively inhibit the enzyme: nucleoside analogs and non nucleoside inhibitors. MPA is of the second class and binds the NAD site within the enzyme. Nucleoside analog inhibitors bind to the IMP substrate site. Accordingly, it was asked whether one could detect synthetic lethality when nucleoside analog inhibitors were applied to Clone 12 cells. In this assay two drugs were screened, mizoribine and ribavirin, both in use against viral infections. Both drugs were tested on Clone 12 cells grown in 96 well microtiter plates in serial dilutions of the drugs as well as serial dilutions of guanine. The observed matrices of results with mizoribine and ribavirin are shown in FIGS. 7 and 8, respectively. Both drugs caused retention of the survival plasmid, in a way that was dependent on the concentration of each drug as well as that of guanine. These matrices allowed sensitive measurement of the synthetic lethal effects imposed by these nucleoside analogs.

The next step was to test the synthetic lethality assay in a blind test. IMPDH inhibitors were screened. Clone 12 was seeded into 1200 wells in microtiter plates in medium lacking selection. MPA, ribavirin, mizoribine, and hygromycin B were added at random (together with guanine) to three wells. Alanosine, an inhibitor of adenylosuccinate synthase (an enzyme in the pathway converting IMP to AMP) was also added as a negative control. As expected, the survival plasmid was not retained in the presence of alanosine (data not shown). However, the presence of all three IMPDH inhibitors and hygromycin B was clearly detected as were two wells containing false positive cells (FIG. 9). The calculated false positive rate for this experiment was 1/600 and was similar to previous control experiments (data not shown).

These results demonstrate the feasibility of a synthetic lethality screen in cultured human cells, using a sensitive fluorescent assay allowing detection of synthetic lethality imposed with a chemical reagent.

VI. Rodent Model of Synthetic Lethality

Autonomous replication of a survival plasmid in rodent cells may be conferred by either the EBV-based pREP/pCEP vectors described above, or by the polyoma virus origin of DNA replication together with the virus segment encoding the large T antigen (Z. Zhu et al., J. Virol. 51,170 (1984). We have found that the EBV-based survival plasmid described above can be used in mouse cells for chemical synthetic lethality screening much as described above with respect to the human system (our unpublished results).

Genetic Synthetic Lethality Screening Experimental Procedures

I. Construction of Plasmids.

pIS was constructed by replacing the BamHI fragment encoding CD20 from pCMV-CD20 with a blunt-ended HindIII-BamHI fragment containing the coding sequence of sphGFP from the pGFPsph-b [R] vector (Packard Instruments). The dominant selectable marker encoding resistance to zeocin (zeo$^R$)was initially excised (together with a synthetic bacterial promoter) from pVgRXR (Invitrogen) by PstI and SalI restriction enzymes. The zeo$^R$ gene was introduced into a mammalian transcription unit by substitution of the neo$^R$ gene present in pREP9 (Invitrogen) in between the Bgl II and Rsr II restriction sites. The generated plasmid product was cleaved by PflMI and BstEII restriction endonucleases, and the excised zeo$^R$ transcription unit, replaced a HindIII and XbaI flanked neo$^R$ gene present in the original pIS vector. The episomal HPRT1-tpzGFP survival plasmid was previously described.

II. Construction of Truncated Sense and Antisense cDNA Library.

The guanosine monophosphate synthetase (GMPS; EC 6.3.5.2) cDNA coding region was obtained by PCR amplification of cDNA from the SL.1NFLS human fetal spleen/liver cDNA libraiy (Research Genetics). The primers for GMPS cDNA were SEQ ID No. 1: 5'-ACATCCCATGGCTCTGTGCAACGG-3' and SEQ ID No. 2: 5'-GCATCCCGGGTTACTCCCACTCAGTAG3'. The 2082 bp GMPS cDNA PCR product subcloned into pBluescript SK+ (Stratagene). 5 µg of this insert were excised and treated with DNase I (Worthington) in 50 mM Tris-HCl pH 8, 10 mM MnCl$_2$, and 0.005 units DNase I in a 50 µl reaction, until fragments were estimated to be at an average length of 300 bps. The reaction was stopped by adding an equal volume of. phenol/chloroform, extraction, and ethanol precipitation. The DNA fragments were then blunted using T4 DNA polymnerase (New England Biolabs).

The adaptor encoding initiating ATG in all three reading frames, and a HindIII recognition sequence, was prepared by annealing the oligonucleotides SEQ ID No. 3: P1–5'AAACAAGCTfACCATGGATGGATGG-3' and SEQ ID No. 4: P2–5'-CCATCCATCCATGGTAAGCTTG-3'. The adaptor with a translation termination codon in all three reading frames and a XhoI recognition sequence, was prepared by annealing oligonucleotides SEQ ID No.5: P3-5'-TAGTTAGTTAGCTCGAGTGC-3' and SEQ ID No. 6: P4–5'-AAAGCACTCGAGCTAACTAACTA-3'. Ligation of the cDNA fragments to the adaptors was carried out overnight at 16° C. with T4 DNA ligase (New England Biolabs). The ligated fragments were then PCR amplified using primers P1 and P4. PCR products were digested with XhoI and HindIII, electrophoresed, and products that were larger than 100 bps in length were excised/extracted from agarose gels, and then subcloned into pREP9 (Invitrogen), the former site being proximal to the RSV promoter. Library DNA was prepared from several thousands bacterial colonies.

III. Transfection and Expression of Constructs in Cells.

HPRT1-deficient HT1080 fibrosarcoma cells were maintained in Dulbecco's modified eagle medium (DMEM) supplemented with 10% fetal calf serum (FCS) and 4 mM L-glutamine. All transfections were carried out using Lipofectamine Plus (Life Technologies) according to manufacturer's instructions. For pIS, selection in zeocin (Cayla) was at 500 µg/ml. For the HPRT1-tpzGFP survival plasmid, selection in hygromycin B (Sigma) was carried out at 450 µg/ml, while maintenance was at 50 µg/ml. Selection and maintenance of the pREP9-containing cDNA fragments was at 500 µg/ml and 400 µg/ml G418, respectively. During the selection for GSEs, or verification of their action, besides G418, guanine was added at 100 µM concentration and the hygromycin B selection for the survival plasmid removed.

IV. Fluorescent Scanning of Microtiter Plates and FACS Sorting

For fluorescent scanning, cells were trypsinized and distributed at 30,000 cells/well into 96 well microplates (TPP). Growth medium was changed twice a week and plates were maintained for up to 75 days. Cells remained viable over the entire time period. Prior to scanning, the medium in the microplates was replaced with Hank's balanced salt solution without phenol red. This procedure greatly minimized background fluorescence from the growth medium while maintaining maximal viability. Plates were scanned with a Fluoroskan Ascent CF microplate fluorescence reader using the Ascent software (Labsystems). Excitation for sphGFP was at 390 nm, while emission was measured at 510 nm. Excitation of tpzGFP was at 485 nm, while emission was measured at 527 nm. Integrated sphGFP was used as an internal control for the number of cells. This was achieved by dividing the relative fluorescence resulting from the episomal tpzGFP vector by the relative fluorescence for sphGFP for each well. Cells were returned to growth medium immediately following scanning.

Sorting was carried out using a FACS Star Plus (Becton Dickinson) flow cytometer. Cells were maintained in Hank's balanced salt solution to maintain viability. Sorted cells were immediately lysed in order to extract low molecular weight DNA (B. Hirt, . . . ). Plasmids from the extract were transformed into bacteria and selected for ampicillin resistance.

V. In vitro Enzyme Activity.

Cell lysates were prepared by resuspension of cells in 200 mM Tris-HCl pH 7.5, 200 mM NaCl, 5 mM MgCl$_2$, 1 mM EGTA, 2 mM DTT and 1 mM PMSF, followed by three cycles of freeze-thaw and centrifugation in a microfuge at 14,000 RPM at 4° C. Protein concentration of supernatants was measured using the Bradford method where the average of three separate samples of each lysate was determined.

GMPS activity was measured by a modification of J. Nakamura . . . This was carried out with 40 µg of protein in 30 µl reactions containing 75 mM Tris-HCl pH 7.8, 10 mM MgCl$_2$, 2 mM ATP, 5 mM L-glutamine, 10 mM DTT, 0.266 mM XMP and 33 µM [14C]-8-XMP (Moravek). Reactions were carried out at 40° C. for one hour and terminated by adding 6 µl of 0.25 mM EDTA. 4 µl of the reactions were diluted in 25 ml water and 2 µg each of XMP and GMP was added. This mixture was spotted onto PEI-cellulose UV$_{254}$ TLC plates (Machery-Nagel). Plates were chromatographed in 2M formic acid, dried and scanned with a Fuji phosphorimager. Enzyme activity was calculated as percent conversion of XMP to GMP.

Results

I. Design of the Genetic Synthetic Lethality Screening System

As a model system for the establishment of genetic synthetic lethality, the purine biosynthesis pathway was chosen (FIG. 1). This pathway was successfully utilized in the chemical synthetic lethality system. Biosynthesis of the essential metabolite GMP is achieved in fibroblasts by either the de novo pathway, or when needed, via the human salvage enzyme HPRT1. In the HPRT1-deficient variant of the HT1080 cell line, chemicals such as mycophenolic acid which inhibit the IMP dehydrogenase enzyme (IMPDH; EC 1.1.1.205) disrupt the de novo pathway, thus leading to synthetic lethality. The above experiment show that such selective pressure imposes the retention of an otherwise unstable EBV-based episomal plasmid expressing the HPRT1 cDNA, serving as the gene of interest. In order to test whether the screening for synthetic lethal chemicals could be extended into a genetic screen the activity of GMPS, which should be synthetic lethal with HPRT1- deficiency was tested. In yeast, mutant genes that are synthetic lethal to a mutant gene of interest, are identified by a two step process: first, mutagenizing the endogenous chromosomal genes with a chemical mutagen, which lead to retention of the survival plasmid when synthetic lethality occurs. Second, ectopic expression in the latter recipients of the wild-type counterparts for the synthetic lethal genes (present in a normal yeast genomic library), leading to relief of the survival plasmid retention. In human cells, an alternate method was used, in which abrogation of cellular gene activity is achieved by expression of dominant-negative genetic suppressor elements contained within a library made of truncated sense or antisense cDNAs for human GMPS. The library itself was incorporated into an episomal expression vector that can be easily rescued. Selection should be achieved if a dominant-negative GSE decreases the enzymatic activity of the resident GMPS, leading to retention of the HPRT1-encoding episomal survival plasmid marked by tpzGFP. Efficient isolation of cells displaying high tpzGFP-emitted flourescence is enabled by FACS sorting. As compared with the yeast method, this system couples the "mutagenesis" step with sequence identification of the affected target in one step.

II. Setting up of the Experimental System

Cells for this screen were prepared by stable integration of pIS (FIG. 10A) which encodes the sapphire green fluorescent protein (sphGFP) and the bacterial zeocin resistance (zeo$^R$) DNA into the HPRT1$^{-/-}$ variant of the HT1080 fibrosarcoma cell line. Stable cell clones were examined by fluorescent light microscopy and using a fluorescence plate reader. SphGFP fluorescence is used as internal marker normalizing the fluorescence readings originating from the episomal survival vector, to cell number. After selection of a stable cell clone, the HPRT1-tpzGFP survival plasmid (FIG. 10B) was transfected into the chosen clone. This episomal vector carries the ColE1 ori, Amp$^R$, the cDNA encoding HPRT1, tpzGFP, hygromycin B resistance gene (hyg$^R$), and the Epstein-Barr viral protein EBNA-1 that together with the viral oriP element is necessary for the replication and episomal state of the plasmid. A stable cell clone, Clone 13 was chosen as the recipient of choice for GSE library. This clone retains tpzGFP fluorescence when grown under hygromycin B selection and this fluorescence decays to less than 1% when cells are grown without hygromycin B for a period of one month (data not shown).

Figure 10C:
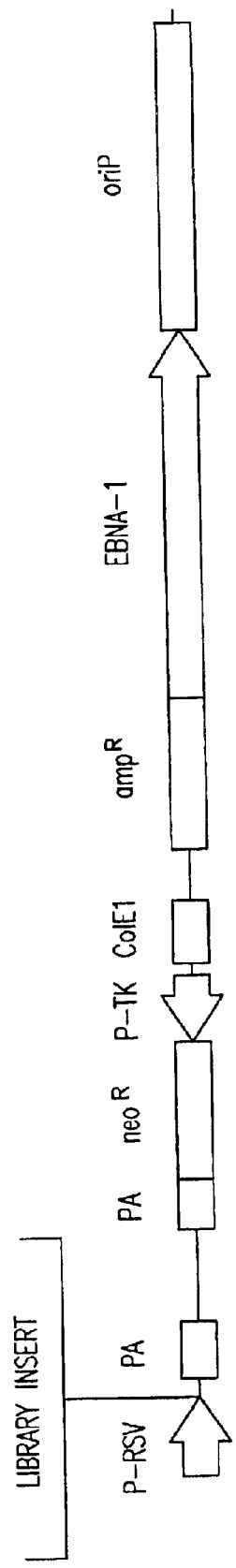

A library consisting of random DNase I generated fragments of the coding region of the GMPS cDNA was constructed. These fragments were ligated to adaptors that encode for an initiating AUG in all three reading frames, and an adaptor encoding a termination codon in all three reading frames. These adaptors also carried restriction sites for insertion of the library into an episomal vector pREP9 that also encodes for neomycin resistance (neo$^R$). The library fragments were then amplified using PCR, size selected for length above ~100 base pairs, cut with the appropriate restriction enzymes, and inserted into the episomal vector (FIG. 10C). Library DNA represented several thousand separate bacterial colonies.

III. Selection for GSEs via Synthetic Lethality Screen

Clone 13 cells were transfected with DNA from the library, and hygromycin B selection was removed, allowing spontaneous loss of the survival plasmid. Selection of stable library transfected cells was carried out with G418 together with 100 μM of guanine. The presence of guanine in the growth medium is necessary so that the salvage enzyme HPRT1, encoded by the survival plasmid, could efficiently produce GMP, in case a GSE blocked the activity of GMPS. After the initial selection period the cells were grown as a pool of transfectants in the presence of G418 and guanine. Pools of cells were maintained by trypsinization and reseeding over a period of 7 weeks. TpzGFP fluorescence was periodically monitored using a fluorescence microscope and by FACS.

Figure 11C:
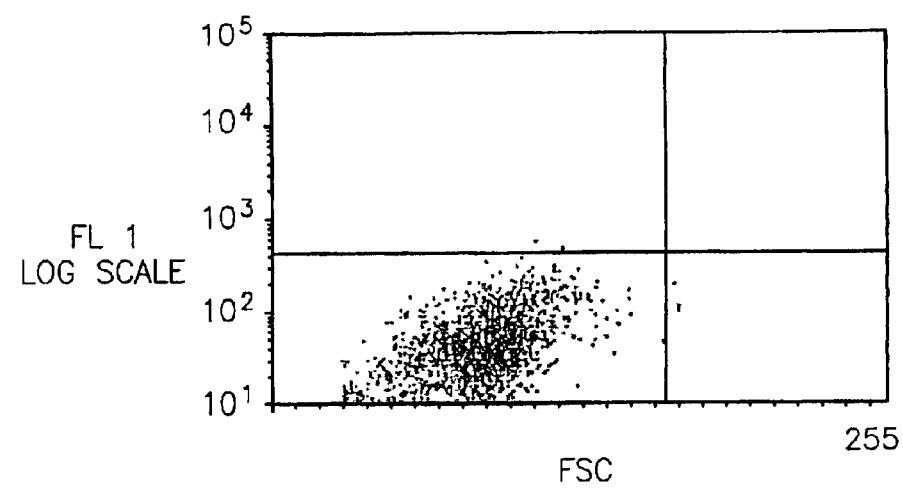

Highly fluorescent cells were then sorted by FACS. In contrast to Clone 13 cells kept continuously under hygromycin B selection pressure (FIG. 11A), the population of library transfected cells retaining tpzGFP fluorescence was approximately 2% of the total population (FIG. 11C). This small percentage of fluorescent cells was not detectable in Clone 13 cells that were grown for the same period of time without hygromycin B (FIG. 11B), where virtually all cells had lost fluorescence. A total of 240,000 cells were separated by FACS sorting (FIG. 11C).

Episomal DNA was extracted from the sorted cells and consequently transformed into DH10B bacteria. In order to distinguish between rescued survival plasmid and plasmids harboring putative GSEs, ampicillin resistant bacterial colonies were hybridized to the GMPS cDNA.

The inserts of 9 plasmids were sequenced. FIG. 12 shows the distribution of the putative GSEs derived from the GMPS library. The distribution of the putative GSEs revealed a certain bias to the N and C termini of the GMPS open reading frame (ORF). However, two fragments also originated from the center of the ORF. A number of single base pair mutations were present in the putative GSE sequences. These mutations were most likely introduced by Taq polymerase during the PCR amplification step of the library making. Validation of dominant-negative activity of the putative GSEs was determined by reintroducing separately each of the rescued GSE-containing plasmids into Clone 13 cells. These secondary transfections were carried out in similar conditions to the primary library transfection, and pools of stable transfectants were grown as separate cell lines. Verification that these putative GSEs could force retention of the HPRT1-encoding survival plasmid was accomplished by seeding cells into 96 well microtiter plates in medium with or without G418. In the presence of G418, the episome encoded GSE is retained. If the GSE encodes for a dominant-negative GMPS activity, one would expect retention of the survival plasmid and concomitant high tpzGFP to sphGFP fluorescence ratio. Without G418, loss of the putative GSE should allow loss of the survival plasmid and decay of the tpzGFP fluorescence. All clones, except one, retained high tpzGFP fluorescence over time, while tpzGFP fluorescence was lost without G418 (data not shown). One putative GSE, truncated sense #5 (182 S in FIG. 12), did not cause retention of the survival plasmid and therefore tpzGFP fluorescence decayed both with and without G418. The kinetics of tpzGFP loss in GSE #5 was similar to Clone 13 when removed from hygromycin B selection.

In order to further verify the dominant-negative nature of the GSEs, separate transfections of the plasmids were carried out again, so that fresh, stably transfected pools of cells could be measured for in vitro GMPS enzyme activity. Cells maintained with G418 and guanine were harvested three weeks after transfection, and protein lysates were prepared. Table 2 shows the average of three GMPS activity assays performed with cell lines of pooled stable transformants expressing the GMPS GSEs. Values were expressed as percent activity when compared to GSE #5, which was used as a negative baseline control. GMPS activity was significantly low in all cell lines, with activity values in the range of 34 to 73% of that displayed by GSE #5. In the GMPS activity assays, enzyme activity of the HT1080 parental cells and Clone 13 recipient cells was also examined (data not shown), and was comparable to that found in GSE #5.

Two additional controls have been performed. In one, stable introduction of the characterized GMP synthetase GSEs into another human cell line (U2-OS) was shown, resulted in decreased enzymatic activity of the resident enzyme. Secondly, expression of the same GSEs in the HPRT1-deficient HT1080 cells (in the absence of the survival plasmid), led to cell death/growth inhibition (data not shown). The latter strongly supprtsthe contention for GMPS GSEs mediated synthetic lethality with HPRT1-deficiency.

References

1. Bender and J. R. Pringle, Mol. Cell. Biol. 11,1295 (1991);
2. V. Doye and E. C. Hurt, Trends Genetics 11,235 (1995);
3. Koshland, D. et al, Cell 40,393 (1985);

TABLE 2

GMPS activity in lysates of Clone 13 cells stably transfected with GMPS GSEs.

| GSE | Type[1] | Position in GMPS | Average Activity (%)[2] | StDev (% |
|---|---|---|---|---|
| 9 | S | 1–122 | 52.57 | 7.16 |
| 11 | S | 1–122 | 41.76 | 9.57 |
| 8 | S | 1–292 | 56.03 | 13.69 |
| 3 | S | 1–322 | 59.23 | 12.57 |
| 1 | AS | 617–871 | 33.89 | 5.22 |
| 10 | S | 865–1159 | 39.71 | 16.93 |
| 4 | S | 1748–2082 | 73.33 | 10.07 |
| 2 | AS | 1951–2082 | 41.45 | 6.85 |

[1]Type refers to sense orientation (S) or antisense orientation (AS) of GSE.
[2]Average activity is the average of three independent experiments and is expressed as percentage of GSE 5 (1–182 bp Sense) activity.

What is claimed is:

1. A method for screening a molecule, wherein said molecule is a chemical compound, or a drug which has a synthetic lethal property, when in combination with a gene of interest carrying a non-lethal mutation, said method comprising the steps of:
   i. transfecting a first reporter gene, as part of an integration plasmid, into mammalian cells having a genome comprising a gene of interest which carries a non-lethal mutation, or a genome which is null of said gene of interest;
   ii. selecting clones stably expressing said first reporter gene;
   iii. introducing into said cells a survival plasmid comprising a functioning copy of said gene of interest, a second reporter gene, selectable marker, an origin of DNA replication and a nuclear antigen gene essential for replication of the plasmid within said cells, wherein said survival plamid is autonomously replicating and spontaneously lost from said cells;
   iv. growing said cells in the presence of a selection compound which selects for said selectable marker;
   v. selecting cell clones stably expressing said second reporter gene and said functioning copy of said gene of interest;
   vi. removing said selection compound, which selects for said selectable marker, and adding molecules destined for screening of their ability to impose selective pressure enforcing retention of the unstable survival plasmid.
   vii. determining survival plasmid retention in cells by measuring the expression ratio of second's to first reporter gene, wherein, if the survival plasmid retains; the molecule has a synthetic lethal property when in combination with a non lethal mutated gene of interest.

2. The method according to claim 1, wherein said selectable marker is a dominant selectable marker.

3. The method according to claim 1, wherein said cells are human cells.

4. The method according to claim 1, wherein said cells are rodent cells.

5. The method according to claim 1, wherein the products of said first reporter gene and second reporter gene are fluorescent proteins.

6. The method according to claim 5, wherein the product of said first reporter gene has an excitation and/or emission peak which differs from the excitation and or emission peak of the product of said second reporter gene.

7. The method according to claim 3, wherein said human cells are human cancer cells.

8. The method according to claim 7, wherein said gene of interest is specifically incapacitated in human cancer cells.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: human

<400> SEQUENCE: 1
acatcccatg gctctgtgca acgg                                          24

<210> SEQ ID NO 2
<211> LENGTH: 27
<212> TYPE: DNA
<213> ORGANISM: human

<400> SEQUENCE: 2
gcatcccggg ttactcccac tcagtag                                       27

<210> SEQ ID NO 3
<211> LENGTH: 25
<212> TYPE: DNA
<213> ORGANISM: human

<400> SEQUENCE: 3
aaacaagctt accatggatg gatgg                                         25

<210> SEQ ID NO 4
<211> LENGTH: 22
<212> TYPE: DNA
<213> ORGANISM: human

<400> SEQUENCE: 4
ccatccatcc atggtaagct tg                                            22
```

```
-continued

<210> SEQ ID NO 5
<211> LENGTH: 20
<212> TYPE: DNA
<213> ORGANISM: human

<400> SEQUENCE: 5
tagttagtta gctcgagtgc                                           20

<210> SEQ ID NO 6
<211> LENGTH: 23
<212> TYPE: DNA
<213> ORGANISM: human

<400> SEQUENCE: 6
aaagcactcg agctaactaa cta                                       23
```